United States Patent
Chung et al.

(10) Patent No.: US 7,893,315 B2
(45) Date of Patent: Feb. 22, 2011

(54) DERIVATION OF EMBRYONIC STEM CELLS AND EMBRYO-DERIVED CELLS

(75) Inventors: Young Gie Chung, Shrewsbury, MA (US); Robert Lanza, Clinton, MA (US); Irina V. Klimanskaya, Upton, MA (US)

(73) Assignee: Advanced Cell Technology, Inc., Marlborough, MA (US)

( * ) Notice: Subject to any disclaimer, the term of this patent is extended or adjusted under 35 U.S.C. 154(b) by 0 days.

(21) Appl. No.: 11/800,366

(22) Filed: May 3, 2007

(65) Prior Publication Data

US 2008/0057041 A1 Mar. 6, 2008

Related U.S. Application Data

(63) Continuation-in-part of application No. 11/267,555, filed on Nov. 4, 2005.

(60) Provisional application No. 60/726,775, filed on Oct. 14, 2005, provisional application No. 60/723,066, filed on Oct. 3, 2005, provisional application No. 60/687,158, filed on Jun. 3, 2005, provisional application No. 60/662,489, filed on Mar. 15, 2005, provisional application No. 60/624,827, filed on Nov. 4, 2004, provisional application No. 60/839,622, filed on Aug. 23, 2006, provisional application No. 60/831,698, filed on Jul. 17, 2006, provisional application No. 60/798,065, filed on May 4, 2006, provisional application No. 60/797,449, filed on May 3, 2006.

(51) Int. Cl.
  C12N 5/05 (2006.01)
  C12N 5/08 (2006.01)
  A61K 35/14 (2006.01)

(52) U.S. Cl. .......................... 800/21; 435/366; 435/325

(58) Field of Classification Search .................. 800/21; 435/366, 325
See application file for complete search history.

(56) References Cited

U.S. PATENT DOCUMENTS

| | | |
|---|---|---|
| 2002/0022268 A1 | 2/2002 | Xu et al. |
| 2002/0035735 A1 | 3/2002 | Schatten et al. |
| 2003/0087859 A1 | 5/2003 | Kochanek et al. |
| 2004/0199935 A1 | 10/2004 | Chapman |
| 2004/0229350 A1* | 11/2004 | Strelchenko et al. ........ 435/366 |
| 2005/0118713 A1 | 6/2005 | Strelchenko et al. |
| 2005/0138680 A1 | 6/2005 | Lee et al. |
| 2005/0265976 A1 | 12/2005 | Cibelli et al. |
| 2006/0014278 A1 | 1/2006 | Khillan |
| 2006/0206953 A1 | 9/2006 | Lanza et al. |
| 2007/0298496 A1* | 12/2007 | Kuo et al. ................ 435/377 |

FOREIGN PATENT DOCUMENTS

| | | |
|---|---|---|
| WO | WO 95/17500 | 6/1995 |
| WO | WO-01/50848 | 7/2001 |
| WO | WO-03/018760 | 3/2003 |
| WO | WO-2005/070011 | 8/2005 |
| WO | WO-2006/013519 | 2/2006 |
| WO | WO-2006/013573 | 2/2006 |
| WO | WO 2006/052646 | 5/2006 |
| WO | WO-2006/080952 | 8/2006 |
| WO | WO-2007/130664 | 11/2007 |

OTHER PUBLICATIONS

Robertson 1987, Embryo-derived stem cells, Teratocarcinomas and Embryonic Stem cells. IRL Press Oxford. pp. 71-112.*
Robertson 1987, Embryo-derived stem cells, Teratocarcinomas and Embryonic Stem cells. IRL Press Oxford. pp. 113-151.*
Khillan JS et al., A simple and convenient method for preparing chimeric animals from embryonic stem (ES) cells. Transgenic Res. Dec. 2003;12(6):739-41.*
Senger. Pathways to Pregnancy and Parturition. Current Concepts, Inc.:Pullman, 1997. Chapter 13, p. 221-222.*
Becker and Chung, "Embryonic stem cells from single blastomeres," Methods Enzymol. 2006; 418:108-16.
Chung, et al., Embryonic and extraembryonic stem cell lines derived from single mouse blastomeres, *Nature* (2006) 439:216-0.
Cowan et al., Derivation of embryonic stem-cell lines from human blastocysts, N. Engl J. Med. 350:1353-1356 (2004).
Evans et al., Establishment in culture of pluripotential cells from mouse embryos Nature, 292:154-156 (1981).
Geber et al., Blastomere development after embryo biopsy: a new model to predict embryo development and to select for transfer. Hum. Reprod. Mar. 1999;14(3):782-6.
Geber, S., et al., Proliferation of blastomeres brom biopsied cleavage stage human embryos in vitro: an alternative to blastocyst biopsy for preimplantation diagnosis. Human Reproduction. 10:1492-1496 (1995).
Klimanskaya et al., "Human embryonic stem cell lines derived from single blastomeres," Nature Nov. 23, 2006:444 (7118):481-5.
Mitalipov et al., "Development of rhesus monkey demi-embryos created by blastomere separation at the 2-cell stage," Theriogenology 2000, v. 53, p. 397.
Papioannou (In Joyner, A. L 2nd ed, Gene Targeting a practical approach, Oxford University Press, Oxford pp. 107-146.
Rani et al., "A Simple and Convenient Method for Preparing Chimeric Animals from Embryonic Stern (ES) Cells" Transgenic Research, 2003, 739-741.
Schraermeyer et al., "Subretinally transplanted embryonic stem cells photoreceptor cells from degeneration in the RCS rats" Cell Transplant, 2001. vol. 10, No. 8, pp. 673-680.
Sills, et al., "Identification and isolation of embryonic stem cells in reproductive endocrinology: theoretical protocols for conservation of human embryos derived from in vitro fertilization," Theoretical Biology and Medical Modeling, 2005,2:25, 1-8.

(Continued)

*Primary Examiner*—Thaian N Ton
*Assistant Examiner*—Marcia S Noble
(74) *Attorney, Agent, or Firm*—Hunton & Williams LLP

(57) ABSTRACT

This present invention provides novel methods for deriving embryonic stem cells and embryo-derived cells from an embryo without requiring destruction of the embryo. The invention further provides cells and cell lines derived without embryo destruction, and the use of the cells for therapeutic and research purposes. It also relates to novel methods of establishing and storing an autologous stem cell line prior to implantation of an embryo, e.g., in conjunction with reproductive therapies such as IVF.

26 Claims, 8 Drawing Sheets

OTHER PUBLICATIONS

Thomson et al., Embryonic stem cell lines derived from human blastocysts, Science, 282:1145-1147 (1998).

Van de Velde H. et al., Embryo implantation after biopsy of one or two cells from cleavage-stage embryos with a view to preimplantation genetic diagnosis. Prenat. Diagn. Dec. 2000;20(13):1030-7.

Wilton et al., "Biopsy of preimplantation mouse embryos: development of micromanipulated embryos and proliferation of single blastomeres in vitro," Biol Reproduction, Jan;40(1):145-52, 1989.

Delhaise, F., et al., "Establishment of an Embryonic Stem Cell Line from 8-Cell Stage Mouse Embryos," European Journal of Morphology, 34(4):237-243 (1996).

Geber, S., et al., "Blastomere Development After Embryo Biopsy: A New Model to Predict Embryo Development and to Select for Transfer," Hum. Reprod., 14(3):782-786 (1999).

Klimanskaya, I., et al., "Derivation Of Human Embryonic Stem Cells From Single Blastomeres," Nature Protocols, 2(8):1963-1972 (2007).

Supplementary European Search Report dated Aug. 6, 2008 for EP 05 81 9524.

Wade, N. "Stem Cell Test Tried on Mice Saves Embryo." New York Times, Oct. 17, 2005, available on-line at http://www.nytimes.com/2005/10/17/health/17stem.html?pagewanted=print.

Fong et al., Unsuccessful derivation of human embryonic stem cell lines from pairs of human blastomeres, Reprod Biomed Online. Aug. 2006;13(2):295-300.

Stem Cell: Scientific Progress and Future Research Directions, Department of Health and Human Services, Chapter 1: The Cell, Jun. 2001, pp. 1-4, </info/scireport/2001report>.

Bradley, Production and analysis of chimaeric mice, Teratocarcinomas and Embryonic Stem Cells (1987) IRL Press Oxford, pp. 113-151.

Van de Velde, The four blastomeres of a 4-cell stage human embryo are able to develop individually into blastocysts with inner cell mass and trophectoderm, Human Reproduction, 2008, vol. 23:8, pp. 1742-1747.

Wakayama, Efficient Establishment of Mouse Embryonic Stem Cell Lines from Single Blastomeres and Polar Bodies, Stem Cell, 2007, vol. 25, pp. 986-993.

Solter, Immunosurgery of mouse blastocyst, Proc. Nat. Acad. Sci., Dec. 1975, vol. 72(12), pp. 5099-5102.

Schuldiner, Selective Ablation of Human Embryonic Stem Cells Expressing a "Suicide" Gene, Stem Cell, 2003, vol. 21, pp. 257-265.

Ogawa, A novel mechanism for regulating clonal propagation of mouse ES cells, Genes to Cell, 2004, vol. 9, pp. 417-477.

Harvey, Inducible control of gene expression: prospects for gene therapy, Current Opinion in Chemical Biology, 1998, vol. 2, pp. 512-518.

Springer, Prodrug-activating systems in suicide gene therapy, The Journal of Clinical Investigation, May 2000, vol. 105(9), pp. 1161-1167.

Thomson, Isolation of a primate embryonic stem cell line, Proc. Natl. Acad. Sci., Aug. 1995, vol. 92, pp. 7844-7848.

Andrews, From teratocarinomas to embryonic stem cells, Phil. Trans. R. Soc. Lond. B, 2002, vol. 357, pp. 405-417.

Ouhibi, Initial Culture Behaviour of Rat Blastocysts on Selected Feeder Cell Lines, Molecular Reproduction and Development, 1995, vol. 40, pp. 311-324.

Wang, et al., "Increases in phosphorylation of SAPK/JNK and p38MAPK correlate negatively with mouse embryo development after culture in different media," Fertil Steril. Apr. 2005;83 Suppl 1:1144-54.

Chesne, et al., "Nuclear transfer in cattle: birth of cloned calves and estimation of blastomere totipotency in morulae used as a source of nuclei," C R Acad Sci III. 1993;316(5):487-91.

Supplementary European Search Report received in EP 07 79 4602 dated Feb. 18, 2010.

* cited by examiner

US 7,893,315 B2

DERIVATION OF EMBRYONIC STEM CELLS AND EMBRYO-DERIVED CELLS

CROSS REFERENCE TO RELATED APPLICATIONS

This application in a continuation-in-part of and claims the benefit of priority to U.S. application Ser. No. 11/267,555, filed Nov. 4, 2005, which claims priority to U.S. Provisional Application Nos. 60/624,827, filed Nov. 4, 2004; 60/662,489, filed Mar. 15, 2005; 60/687,158, filed Jun. 3, 2005; 60/723,066, filed Oct. 3, 2005; and 60/726,775, filed on Oct. 14, 2005. This application also claims the benefit of U.S. Provisional Application Nos. 60/797,449, filed May 3, 2006; 60/798,065, filed May 4, 2006; 60/831,698, filed Jul. 17, 2006, and 60/839,622, filed Aug. 23, 2006. The disclosures of each of the foregoing applications are hereby incorporated by reference in their entirety.

FIELD OF THE INVENTION

This invention generally relates to novel methods for deriving embryonic stem (ES) cells and embryo-derived (ED) cells, those cells and cell lines, and the use of the cells for therapeutic and research purposes. It also relates to novel methods of establishing and storing an autologous stem cell line prior to implantation of an embryo, e.g. in conjunction with assisted reproductive technologies such as in vitro fertilization.

BACKGROUND OF THE INVENTION

With few exceptions, embryonic stem cells have only been grown from blastocyst-stage embryos. ES cell lines are conventionally isolated from the inner cell mass of blastocysts. There are several drawbacks to the techniques used to create these cells. From the perspective of the technique, the culturing of embryos to blastocysts occasionally has a relatively low success rate. Additionally, certain members of the public object to embryonic stem (ES) cell research using cell lines derived from the inner cell mass of blastocysts because this derivation procedure destroys the preimplantation, blastocyst-stage embryo. As such, the blastocyst-stage embryo from which ES cells are conventionally produced cannot be cryopreserved, frozen for later use, or permitted to develop further.

The present invention provides novel methods for deriving ES cells, ES cell lines, and other embryo-derived (ED) cells for use in research and medicine. The methods described herein permit the derivation of ES cells, ES cell lines, and other ED cells from embryos but without the need to destroy those embryos.

SUMMARY OF THE INVENTION

The present invention provides novel methods for deriving embryonic stem cells and embryo-derived cells from an embryo, those cells and cell lines, and uses of the embryonic stem cells and cell lines for therapeutic and research purposes. It also relates to a method of establishing and storing an autologous stem cell line from a blastomere retrieved prior to implantation of an embryo, e.g. in conjunction with assisted reproductive technologies such as in vitro fertilization ("IVF").

In a first aspect, the invention provides a method of producing human embryonic stem (ES) cells. The method generally comprises culturing a blastomere obtained from a human embryo. In certain embodiments, the blastomere is cultured in medium containing less than 5 mM glucose and/or having an osmolarity of less than 310 mosm to generate a cluster of two or more blastomeres. The cultured cluster of two or more blastomeres is contacted (directly or indirectly) with embryonic or fetal cells, and the cluster of two or more blastomeres is then further cultured (in the presence or absence of embryonic or fetal cells) to produce ES cells.

In certain embodiments, the method initially comprises culturing a blastomere obtained from a human embryo for at least one day in medium containing less than 5 mM glucose and/or having an osmolarity of less than 310 mosm.

In certain embodiments, the method is similarly used to produce partially differentiated cells directly from a blastomere without the need to first derive ES cells.

In certain embodiments, the cultured cluster of two or more blastomeres comprises an aggregate of two or more blastomeres, and the aggregate of two or more blastomeres is contacted with embryonic or fetal cells.

In certain embodiments, during or following contact with embryonic or fetal cells, the cluster of two or more blastomeres is cultured in medium containing at least 5 mM glucose and/or having an osmolarity of at least 310 mosm.

In certain embodiments, two or more blastomeres are initially obtained from an embryo, and the two or more blastomeres are initially cultured in medium containing less than 5 mM glucose and/or having an osmolarity of less than 310 mosm. These blastomeres may be from the same or a different embryo, and these blastomeres may be cultured in direct contact with one another or without contact but in the same culture vessel or microdrop.

In certain embodiments of any of the foregoing or following, obtaining the blastomere from a human embryo yields a blastomere and a remaining human embryo, and the remaining human embryo is not destroyed following obtaining the blastomere. In certain embodiments, the remaining embryo is viable. In certain embodiments, the remaining embryo is cultured for one or more days following removal of the blastomere to assess viability. In certain embodiments, the remaining embryo is cryopreserved.

In certain embodiments of any of the foregoing, a blastomere is obtained from a human embryo after compaction of the morula. In certain embodiments, the blastomere is obtained from a human embryo before formation of the blastocoel. In certain embodiments, the blastomere is obtained from a 4-16 cell embryo, a 4-10 cell human embryo, or a 4-8 cell human embryo.

The cluster of two or more blastomeres and the embryonic or fetal cells are directly or indirectly contacted with each other. In certain embodiments, the cluster of two or more blastomeres and the embryonic or fetal cells are not cultured as aggregates. In certain other embodiments, the cluster of two or more blastomeres is indirectly contacted with the embryonic or fetal cells.

In certain other embodiments, the cells (blastomeres, clusters of blastomeres, and/or embryonic or fetal cells) are cultured in microdrop culture.

In certain embodiments, the embryo (for example, a human embryo) was previously frozen and is thawed prior to obtaining the blastomere.

Various methods and combinations can be used to remove a blastomere from an embryo. Preferably, a blastomere is removed without substantially decreasing the viability of the remainder of the embryo. In other words, following removal of a blastomere, the remainder of the embryo can continue to grow. In certain embodiments, the ability to continue to grow and survive in culture for at least one day following blastomere removal indicates that blastomere removal did not substantially decrease viability. In certain embodiments, the blastomere is obtained by partially or completely removing the zona pellucida surrounding the human embryo. In certain other embodiments, the blastomere is obtained by immobilizing the embryo and tapping the immobilized embryo until the blastomere is isolated.

In certain embodiments in which embryonic or fetal cells are used, exemplary embryonic or fetal cells are human cells. In certain embodiments, the human embryonic or fetal cells are selected from human ES cells, human ED cells, human TS cells, human EG cells, placental stem cells, amniotic fluid cell or stem cells, or human embryo carcinoma cells. In certain embodiments, the embryonic or fetal cells are optionally cultured on a fibroblast feeder layer.

In certain embodiments, the blastomere or cluster of two or more blastomeres is cultured with a factor that inhibits differentiation of the ES cells. In certain embodiments, recombinant Oct-4 is introduced into the blastomere or endogenous Oct-4 is activated in the blastomere during a step of culturing the blastomere to produce the human ES cells.

In certain embodiments, the ES cells or cell lines, for example the human ES cells or cell lines, are pluripotent. In certain embodiments, ES cells express one or more ES cell marker proteins selected from any of Oct-4, alkaline phosphatase, SSEA-3, SSEA-4, TRA-1-60 and TRA-1-81.

In certain embodiments, the blastomere undergoes cell division and one progeny cell is used for genetic testing and a different progeny cell is used to produce human ES cells.

In certain embodiments of any of the foregoing, the method further comprises isolating the ES cells derived from the blastomere and culturing the ES cells to generate an ES cell line.

In another aspect, the invention provides a method of generating autologous stem cells concomitantly to performing genetic diagnosis. A blastomere is removed from an embryo, as is typically done during pre-implantation genetic diagnosis (PGD). The blastomere is cultured and permitted to divide at least once. After division, one progeny cell is used for genetic diagnosis, and the other progeny cell is further cultured (using any of the methods described herein) to produce an ES cell or ES cell line. Such ES cell or ES cell lines would be a suitable source of autologous cells and tissue for the embryo or individual that resulted from that embryo.

In another aspect, the invention provides human ES cells derived from a human embryo but without destroying the human embryo. In certain aspects, the ES cells are produced using any of the methods described herein.

In another aspect, the invention provides a human ES cell line derived from a human embryo but without destroying the human embryo. In certain aspects, the ES cell lines is produced using any of the methods described herein.

In certain embodiments, the human ES cell or ES cell line has one or more characteristics of previously identified, blastocyst-derived ES cell lines. In certain embodiments, the human ES cell or ES cell line is pluripotent and expresses one or more ES cell marker proteins selected from any of Oct-4, SSEA-1, nanog, alkaline phosphatase and Res-1. In certain embodiments, the human ES cell or ES cell line maintains a normal karyotype.

In another aspect, the invention provides a differentiated cell or tissue directly produced from a blastomere.

In another aspect, the invention provides a differentiated cell or tissue derived from a human ES cell or cell line produced from a blastomere. In certain embodiments, the differentiated cell or tissue is lineage committed. In certain embodiments, the differentiated cell or tissue is a mesodermal, endodermal or ectodermal cell or tissue. In certain embodiments, the differentiated cell or tissue is partially or terminally differentiated.

In another aspect, the invention provides a method of producing a desired differentiated cell or tissue by inducing differentiation of a human ES cell or cell line into the desired cell or tissue. In certain embodiments, the method comprises contacting an ES cell or ES cell line produced from a blastomere with one or more agents that promote differentiation of an ES cell or cell line along a particular developmental lineage.

In another aspect, the invention provides compositions and preparations comprising a differentiated cell or tissue produced from an ES cell or cell line derived from a blastomere. In certain embodiments, the compositions and preparations are pharmaceutical preparations formulated in a pharmaceutically acceptable carrier.

In another aspect, the invention provides a method of treating a disorder amenable to cell therapy in a patient by administering an effective amount of an ES cell or cell line produced from a blastomere using any of the methods described herein.

In another aspect, the invention provides a method of treating a disorder amenable to cell therapy in a patient by administering to the patient an effective amount of a differentiated cell or tissue produced either directly from a blastomere culture or produced from an ES cell or cell line.

In another aspect, the invention provides a method of producing a trophoblast stem (TS) cell. The method comprises culturing a blastomere obtained from a human embryo in medium containing less than 5 mM glucose and/or having an osmolarity of less than 310 mosm to generate a cluster of two or more blastomeres; directly or indirectly contacting the cultured cluster of two or more blastomeres to embryonic or fetal cells; and further culturing the cluster of two or more blastomeres until TS cells are produced.

In certain embodiments, method comprises culturing a blastomere obtained from a human embryo for at least one day in medium containing less than 5 mM glucose and/or having an osmolarity of less than 310 mosm.

In certain embodiments, the cultured cluster of two or more blastomeres comprises an aggregate of two or more blastomeres, and the aggregate of two or more blastomeres is contacted with embryonic or fetal cells.

In certain embodiments, during or following contact with embryonic or fetal cells, the cluster of two or more blastomeres is cultured in medium containing at least 5 mM glucose and/or having an osmolarity of at least 310 mosm.

In certain embodiments, the one that one blastomere is initially obtained from an embryo, and the two or more blastomeres are initially cultured in medium containing less than 5 mM glucose and/or having an osmolarity of less than 310 mosm. These blastomeres may be from the same or a different embryo, and these blastomeres may be cultured in direct contact with one another or without contact but in the same culture vessel or microdrop.

In certain embodiments of any of the foregoing or following, obtaining the blastomere from a human embryo yields a blastomere and a remaining human embryo, and the remaining human embryo is not destroyed following obtaining the blastomere. In certain embodiments, the remaining embryo is viable. In certain embodiments, the remaining embryo is cultured for one or more days following removal of the blastomere to assess viability. In certain embodiments, the remaining embryo is cryopreserved.

In certain embodiments of any of the foregoing, a blastomere is obtained from a human embryo after compaction of the morula. In certain embodiments, the blastomere is obtained from a human embryo before formation of the blastocoel. In certain embodiments, the blastomere is obtained from a 4-16 cell embryo, a 4-10 cell human embryo, or a 4-8 cell human embryo.

The cluster of two or more blastomeres and the embryonic or fetal cells are directly or indirectly contacted with each other. In certain embodiments, the cluster of two or more blastomeres and the embryonic or fetal cells are not cultured as aggregates. In certain other embodiments, the cluster of two or more blastomeres is indirectly contacted with the embryonic or fetal cells.

In certain other embodiments, the cells (blastomeres, clusters of blastomeres, and/or embryonic or fetal cells) are cultured in microdrop culture.

In certain embodiments, the embryo (for example, human embryo) was previously frozen and is thawed prior to obtaining the blastomere.

Various methods and combinations can be used to remove a blastomere from an embryo. Preferably, a blastomere is removed without substantially decreasing the viability of the remainder of the embryo. In other words, following removal of a blastomere, the remainder of the embryo can continue to grow. In certain embodiments, the ability to continue to grow and survive in culture for at least one day following blastomere removal indicates that blastomere removal did not substantially decrease viability. In certain embodiments, the blastomere is obtained by partially or completely removing the zona pellucida surrounding the human embryo. In certain other embodiments, the blastomere is obtained by immobilizing the embryo and tapping the immobilized embryo until the blastomere is isolated.

In certain embodiments in which embryonic or fetal cells are used, exemplary embryonic or fetal cells are human cells. In certain embodiments, the human embryonic or fetal cells are selected from human ES cells, human ED cells, human TS cells, human EG cells, placental stem cells, amniotic fluid cell or stem cells, or human embryo carcinoma cells. In certain embodiments, the embryonic or fetal cells are optionally cultured on a fibroblast feeder layer.

In certain embodiments, the method further comprises isolating the TS cells derived from the blastomere. In certain embodiments, the method further comprises establishing a TS cell line from the TS cells derived from the blastomere.

In certain embodiments, exemplary TS cells or TS cell lines express at least one TS cell marker protein selected from the any of cdx-2, fgfr2, PL-1 and human chorionic gonadotropin (hCG). In certain embodiments, exemplary TS cells or TS cell lines do not express Oct-4 or α-feto protein.

In another aspect, the invention provides a human TS cell derived from a human embryo but without destroying the human embryo. In certain embodiments, exemplary TS cells or TS cell lines express at least one TS cell marker protein selected from the any of cdx-2, fgfr2, PL-1 and human chorionic gonadotropin (hCG). In certain embodiments, exemplary TS cells or TS cell lines do not express Oct-4 or α-feto protein.

In another aspect, the invention provides a differentiated cell or tissue derived from a TS cell or TS cell line produced from a blastomere.

In another aspect, the invention provides a method of isolating a blastomere from an embryo. The method comprises immobilizing the embryo and tapping the immobilized embryo until a blastomere is isolated. In certain embodiments, a single blastomere is isolated from the remainder of the embryo. In certain embodiments, multiple blastomeres are isolated from the remainder of the embryo. In certain embodiments, this method is combined with other methods used to obtain a blastomere from an embryo (e.g., removal of the zona pelucida, exposure to enzymes, exposure to Ca2+ and/or Mg2+ free medium). In certain embodiments, the embryo is immobilized using a micropipette. In certain embodiments, the embryo is a 4-16 cell stage embryo, a 4-10 cell stage embryo, or an 8-10 cell stage embryo.

In another aspect, the invention provides a method of conducting embryonic stem cell research without destroying a human embryo. The method comprises obtaining a human ES cell or ES cell line that is derived from a human embryo but without destroying the human embryo. Such lines may be generated using any of the methods for deriving ES cell or cell lines from a blastomere. Once generated, the method further comprises conducting embryonic stem cell research using the human ES cell or ES cell line.

In certain embodiments, conducting embryonic stem cell research comprises contacting the human ES cell or ES cell line with one or more factors, and identifying factors that promote differentiation of the ES cell or ES cell line to one or more mesodermal, endodermal, or ectodermal cell types.

In another aspect, the invention provides a method of producing an embryonic stem (ES) cell. The method comprises culturing a blastomere obtained from a mammalian embryo to generate a cluster of two or more blastomeres; directly or indirectly contacting the cultured cluster of two or more blastomeres with embryonic or fetal cells; and culturing the cluster of two or more blastomeres of (b) until ES cells are produced.

In certain embodiments, the cultured cluster of two or more blastomeres comprises an aggregate of two or more blastomeres, and the aggregate of two or more blastomeres is contacted with embryonic or fetal cells.

In certain embodiments, during or following contact with embryonic or fetal cells, the cluster of two or more blastomeres is cultured in medium containing at least 5 mM glucose and/or having an osmolarity of at least 310 mosm.

In certain embodiments, the one that one blastomere is initially obtained from an embryo, and the two or more blastomeres are initially cultured in medium containing less than 5 mM glucose and/or having an osmolarity of less than 310 mosm. These blastomeres may be from the same or a different embryo, and these blastomeres may be cultured in direct contact with one another or without contact but in the same culture vessel or microdrop.

In certain embodiments of any of the foregoing or following, obtaining the blastomere from a embryo yields a blastomere and a remaining embryo, and the remaining embryo is not destroyed following obtaining the blastomere. In certain embodiments, the remaining embryo is viable. In certain embodiments, the remaining embryo is cultured for one or more days following removal of the blastomere to assess viability. In certain embodiments, the remaining embryo is cryopreserved.

In certain embodiments of any of the foregoing, a blastomere is obtained from a embryo after compaction of the morula. In certain embodiments, the blastomere is obtained from an embryo before formation of the blastocoel. In certain embodiments, the blastomere is obtained from a 4-16 cell embryo, a 4-10 cell embryo, or a 4-8 cell human embryo.

The cluster of two or more blastomeres and the embryonic or fetal cells are directly or indirectly contacted with each other. In certain embodiments, the cluster of two or more blastomeres and the embryonic or fetal cells are not cultured as aggregates. In certain other embodiments, the cluster of two or more blastomeres is indirectly contacted with the embryonic or fetal cells.

In certain other embodiments, the cells (blastomeres, clusters of blastomeres, and/or embryonic or fetal cells) are cultured in microdrop culture.

In certain embodiments, the embryo (for example, a human embryo) was previously frozen and is thawed prior to obtaining the blastomere.

Various methods and combinations can be used to remove a blastomere from an embryo. Preferably, a blastomere is removed without substantially decreasing the viability of the remainder of the embryo. In other words, following removal of a blastomere, the remainder of the embryo can continue to growth. In certain embodiments, the ability to continue to grow and survive in culture for at least one day following blastomere removal indicates that blastomere removal did not substantially decrease viability. In certain embodiments, the blastomere is obtained by partially or completely removing the zona pellucida surrounding the human embryo. In certain other embodiments, the blastomere is obtained by immobilizing the embryo and tapping the immobilized embryo until the blastomere is isolated.

In certain embodiments in which embryonic or fetal cells are used, exemplary embryonic or fetal are mouse cells or human cells. In certain embodiments, the embryonic or fetal cells are from the same species as the blastomere. In certain embodiments, the human embryonic or fetal cells are selected from human ES cells, human ED cells, human TS cells, human EG cells, placental stem cells, amniotic fluid cells or stem cells, or human embryo carcinoma cells. In certain embodiments, the embryonic or fetal cells are optionally cultured on a fibroblast feeder layer.

In certain embodiments, the method further comprises the step of isolating the ES cells derived from the blastomere and generating an ES cell line.

In another aspect, the invention provides a method of producing ES cells. The method comprises obtaining a blastomere from a mammalian embryo; culturing the blastomere to generate a cluster of two or more blastomeres; aggregating the cluster of two or more blastomeres with embryonic or fetal cells; culturing the aggregated cluster of two or more blastomeres and the embryonic or fetal cells until the aggregated cluster of blastomeres exhibits properties of ES cells; and isolating the ES cells derived from the blastomere from the embryonic cells.

In another aspect, the invention provides a method of producing TS cells. The method comprises: obtaining a blastomere from a mammalian embryo; culturing the blastomere to generate a cluster of two or more blastomeres; aggregating the cluster of two or more blastomeres with embryonic or fetal cells; obtaining outgrowths from the cluster of two or more blastomeres, wherein the outgrowths exhibit properties of trophoblast or extraembryonic endoderm cells; contacting the outgrowths with FGF-4 to produce TS cells; and isolating the TS cells derived from the blastomere.

In certain embodiments, the mammalian embryo is a human embryo and the TS cells are human cells. In certain other embodiments, the method further comprises producing a TS cell line by culturing the TS cells derived from the blastomere to produce a TS cell line.

In another aspect, the invention provides a method of producing human embryonic stem (ES) cells. The method comprises: culturing a blastomere obtained from a human embryo in medium containing less than 5 mM glucose and/or having an osmolarity of less than 310 mosm to generate a cluster of two or more blastomeres; directly or indirectly contacting the cultured cluster of two or more blastomeres with medium sufficient to promote the growth and survival of the cultured cluster of two or more blastomeres; and further culturing the cluster of two or more blastomeres to produce ES cells.

In certain embodiment, the method comprises culturing a blastomere obtained from a human embryo for at least one day in medium containing less than 5 mM glucose and/or having an osmolarity of less than 310 mosm to generate a cluster of two or more blastomeres.

In certain embodiments, the medium sufficient to promote the growth and survival of the cultured cluster of two or more blastomeres is medium conditioned with embryonic or fetal cells. In certain other embodiments, the medium sufficient to promote the growth and survival of the cultured cluster of two or more blastomeres is supplemented with ACTH.

In certain aspects, the invention provides a method of producing an embryonic stem cell, comprising the step of culturing a blastomere in embryo medium wherein the blastomere is obtained from an embryo and wherein the embryo remains viable. The method comprises the step of directly or indirectly contacting the cultured blastomere with embryonic stem cells with the proviso that the contacting is not carried out by aggregating the cultured blastomere with embryonic stem cells as had been previously described in Chung et al., Nature (2006) 439:216-9. For example, the cultured blastomere can be cultured in a microdrop and the embryonic stem cells are cultured in separate microdrops. Each microdrop can contain a single blastomere or multiple blastomeres. The microdrop containing the blastomere(s) can be connected to or merged with the microdrop containing the embryonic stem cells using any means known to those of ordinary skill in the art. In one embodiment, the connecting or merging of the two microdrops is carried out by dragging a manipulation pipette between two drops under light mineral oil such as paraffin oil or Squibb's oil.

The method of producing an ES or ED cell may also be used to culture single cells from morula stage embryo, inner cell mass, or embryonic disk, or single embryonic cell or single embryonic germ cell.

In one embodiment, the blastomere is obtained from an embryo prior to compaction of the morula. The entire one cell zygote may be used, though this does not provide the advantage of circumventing the ethical objections some people have to the use of the entire embryo in cell line derivation. Therefore, the preferred method is the use of a donor cell from an embryo between the two cell stage and the blastocyst stage of development. In another embodiment, the embryo is obtained before formation of the blastocoel. The blastomere may be obtained by partial or complete removal of the zona pellucida surrounding the embryo. The biopsied embryo may be implanted or cryopreserved. The initial embryo may have been obtained from oocytes fertilized in vivo or in vitro and may or may not have been previously cryopreserved.

The culture of the blastomere obtained from the embryo is directly or indirectly contacted with cultures of any suitable cell to produce an ES cell line or to produce ED cells, or both. Such suitable cells include, but are not limited to, embryonic stem cells, such as from already established lines, embryo carcinoma cells, embryonic fibroblasts including murine embryonic cells, other embryo-like cells, cells of embryonic origin or cells derived from embryos, many of which are known in the art and available from the American Type Culture Collection, Manassas, Va. 20110-2209, USA, and other sources.

The blastomere may also be cultured with factors that inhibit differentiation of the ES cell derived from the blastomere. Such factors include, without limitation, any factor that blocks or modifies the expression of genes involved in trophoblast development. In one embodiment, the blastomere is cultured in the presence of heparin. In another embodiment, Oct-4 is introduced into the blastomere or alternatively, expression of endogenous Oct-4 is induced in the blastomere.

In another embodiment, a blastomere obtained from an embryo undergoes cell division and one progeny cell is used for genetic testing and another progeny cell is used to produce an ES cell or cell line.

The ES cells produced from the blastomere may be pluripotent or by some definitions totipotent. The degree of pluripotency of the ES cell may be determined by assaying for ES cell marker proteins. Such proteins are known in the art and include Oct-4, SSEA-3, SSEA-4, TRA-1-60, TRA-1-81, and alkaline phosphatase.

The present method of producing an ES or ED cell may be performed on human embryos as well as non-human embryos, e.g., non-human mammalian embryos, other primate embryos, horse embryos, avian embryos or dog embryos.

In another embodiment, the present invention provides a method for producing differentiated progenitor cells, comprising:
 (i) obtaining blastomere cells from an embryo that has at least one cell, preferable two cells, but has not yet developed to the stage of a compacted morula; and
 (ii) inducing differentiation of the blastomere cells to produce differentiated progenitor cells without producing an embryonic stem cell line.

The differentiated progenitor cells can be used to derive cells, tissues and/or organs which are advantageously used in the area of cell, tissue, and/or organ transplantation.

Another aspect of the present invention provides a method for producing differentiated progenitor cells, comprising:
 (i) obtaining blastomere cells from an embryo that has at least one cell, preferably two cells, but has not yet developed to the stage of a compacted morula;
 (ii) culturing the blastomere to obtain an aggregate of more than one cell; and
 (iii) inducing differentiation of the blastomere-derived cells to produce differentiated progenitor cells without producing an embryonic stem cell line.

The differentiated progenitor cells can be used to derive cells, tissues and/or organs which are advantageously used in the area of cell, tissue, and/or organ transplantation.

The present invention also provides methods of differentiating the ES or ED cells produced by the methods of the invention. The ES or ED cells may be differentiated into any cell type including those of mesodermal, endodermal and ectodermal origin. For example, the blastomere may also be cultured with factors that induce differentiation of the ES or ED cell. In one embodiment, the blastomere is cultured in the presence of FGF-4. In some embodiments the ES or ED cell derived from the blastomere is directly differentiated into the desired cell or tissue type without the intermediate state of propagating the undifferentiated ES cells as undifferentiated cell lines.

Also contemplated are methods of differentiating the blastomere obtained from an embryo into a differentiated cell type, e.g., mesoderm, endoderm or ectoderm without first producing an ES cell from the blastomere.

The invention also encompasses the ES or ED cells produced by the methods of this invention, ES cell lines derived from the ES cells, ED cell lines derived from the ED cells, as well as differentiated cells derived from the ES or ED cells or cell lines.

The ES or ED cells provided by this invention or cells derived from the ES or ED cells are useful for treating disorders amenable to cell therapy. Pharmaceutical compositions comprising these cells together with a pharmaceutically acceptable medium or carrier are also provided.

The TS cell produced by the methods of the invention may express a TS cell marker, e.g., fibroblast growth factor receptor 2 (fgfr2), placental lactogen 1 (PL-1) and eomesodermin (mEomes). The TS cell may also lack expression of Oct-4 or α-fetoprotein.

The TS cell may also be cultured to produce a TS cell line or differentiated cell line.

This invention also provides novel methods of isolating blastomeres from an embryo. The method comprises the step of immobilizing the embryo and tapping the immobilized embryo until a blastomere is isolated. The embryo can be immobilized by any means known to those of skill in the art. In one embodiment, the embryo is immobilized using a micropipette and the micropipette holder is tapped to isolate the blastomere. In another embodiment, the embryo is cultured in medium that is calcium and magnesium free. The embryo may be from the 2-cell stage to the 16 cell stage. In one embodiment, the embryo is from the 4 cell stage to the 10 cell stage. In another embodiment the embryo is a 6-8 cell stage embryo. In yet another embodiment, the embryo is an 8-10 cell stage embryo.

In certain embodiments, the invention provides the use of the cell culture as described above in the manufacture of a medicament to treat a condition in a patient in need thereof.

In certain embodiments, the invention provides the use of the pharmaceutical preparation as described above in the manufacture of a medicament to treat a condition in a patient in need thereof.

In certain embodiments of any of the foregoing, a blastomere is obtained from a mammalian embryo. Exemplary mammalian embryos include, but are not limited to, mice embryos, rat embryos, dog embryos, cat embryos, rabbit embryos, cow embryos, sheep embryos, pig embryos, non-human primate embryos, and human embryos. In certain embodiments of any of the foregoing, a blastomere is obtained from a human embryo and the method comprises producing ES cells, ES cell lines, TS cells, TS cell lines, ED cells, or any partially or terminally differentiated cell type thereof.

In certain embodiments of any of the foregoing, a cluster of two or more blastomeres may be directly or indirectly contacted with embryonic or fetal cells. In certain other embodiments, the embryonic or fetal cells are from the same species as the blastomere. In certain embodiments, the embryonic or fetal cells are from a different species as the blastomere. In certain embodiments, the embryonic or fetal cells are human cells. Regardless of the particular embryonic or fetal cells used, the cells may be grown in the presence or absence of feeder layers.

In certain embodiments, contact with embryonic or fetal cells is not necessary. In certain embodiments, a cluster of two or more blastomeres is cultured in the presence of one or more factors sufficient to promote further survival and/or maturation so that ES cells, TS cells, and/or ED cells can be produced from a blastomere.

The invention contemplates various methods for producing ES cells, TS cells, and/or ED cells from a blastomere obtained from an embryo. In certain embodiments, a culture produces a combination of cells types. If desired, one or more particular cell types in the culture can be separated and further cultured to produce a substantially purified population of cells or a cell line.

The invention contemplates combinations of any of the foregoing or following aspects and embodiments of the invention.

BRIEF DESCRIPTION OF THE FIGURES

FIG. 3(a) through 3(g) show immunofluorescence staining for molecular markers for pluripotency: (a) Oct-4 and corresponding DAPI staining (b), (c) TRA-1-60, (d) TRA-1-81, (e) SSEA-3, (f) SSEA-4, (g) alkaline phosphatase (Scale bar, 200 um). FIG. 3(h) shows representative chromosome spreads of the two single-blastomere-derived hES cell lines (MA01 and MA09).

FIG. 4(a) shows teratoma formation after transplantation of the human ES cells under the kidney capsule of NOD-SCID mice for seven weeks. Inserts show enlargement of adjacent sections; left, neural tissue stained for Nestin (ectoderm); center, alpha smooth muscle actin (mesoderm); right, intestine stained for cdx2 (endoderm) to confirm presence of all three germ layers. FIG. 4(b) through 4(d) shows immunofluorescence analysis of molecular markers of (b) ectoderm (tubulin β III), (c) mesoderm (smooth muscle actin), and (d) primitive endoderm (α-feto protein). FIG. 4(e) through (i) show results of in vitro differentiation of single blastomere-derived human ES cells into cells of specific therapeutic interest; (e) endothelial cells plated on Matrigel showing formation of typical capillary tube-like structures, (f) Ac-LDL uptake by endothelial cells, (g) and (h) retinal pigment epithelium (RPE) showing pigmented phenotype and typical "cobblestone" morphology (g) and bestrophin staining (h). FIG. 4(i) shows results of RT-PCR confirming the presence of PEDF (lanes 1 and 2) and RPE65 (lanes 3 and 4) in the human ES cell that was differentiated into RPE cells (Lanes 1 and 3: hES-derived RPE cells; lanes 2 and 4: fetal RPE controls).

FIG. 5(a), (b) and (c) show results of PCR to detect the presence of amelogenin, SRY and eGFP, respectively. FIG. 5(d) shows the results of the microsatellite analysis.

DETAILED DESCRIPTION OF THE INVENTION

Figure 1:
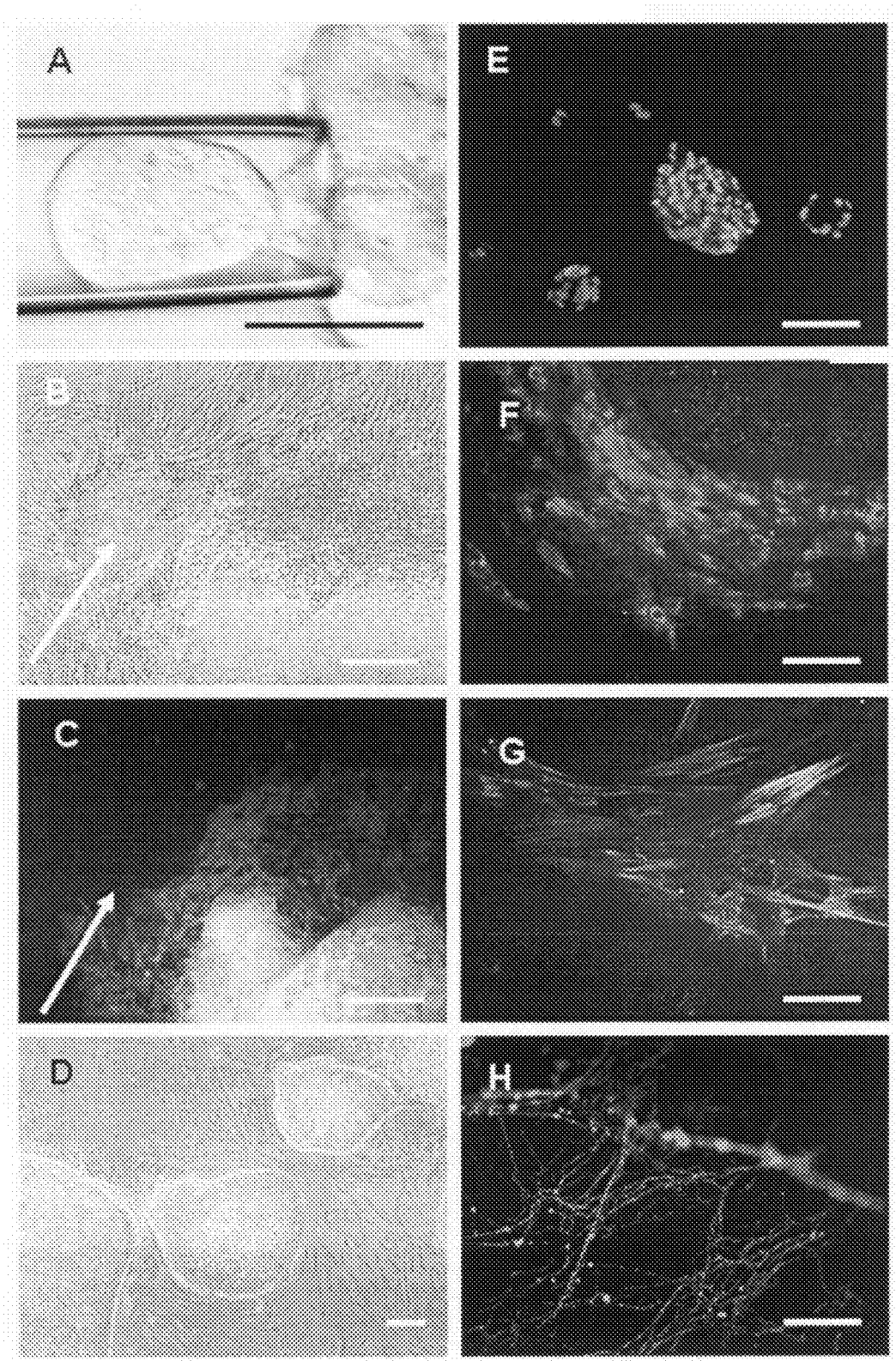
FIG. 1A shows a biopsy of a single human blastomere.
FIGS. 1B-C show blastomere-derived outgrowths (see arrows) close to a colony of GFP-positive human embryonic stem (hES) cells.
FIG. 1D illustrates the morphology of hES cell colonies.
FIG. 1E shows Oct-4 staining in hES cells.
FIGS. 1F-H show immunofluorescence analysis of molecular markers of primitive endoderm (α-feto protein, FIG. 1F), mesoderm (smooth muscle actin, FIG. 1G) and ectoderm (tubulin β III, FIG. 1H). (Scale bar: 50 μm for FIG. 1A; 200 μm for FIG. 1B-H).
Figure 2:
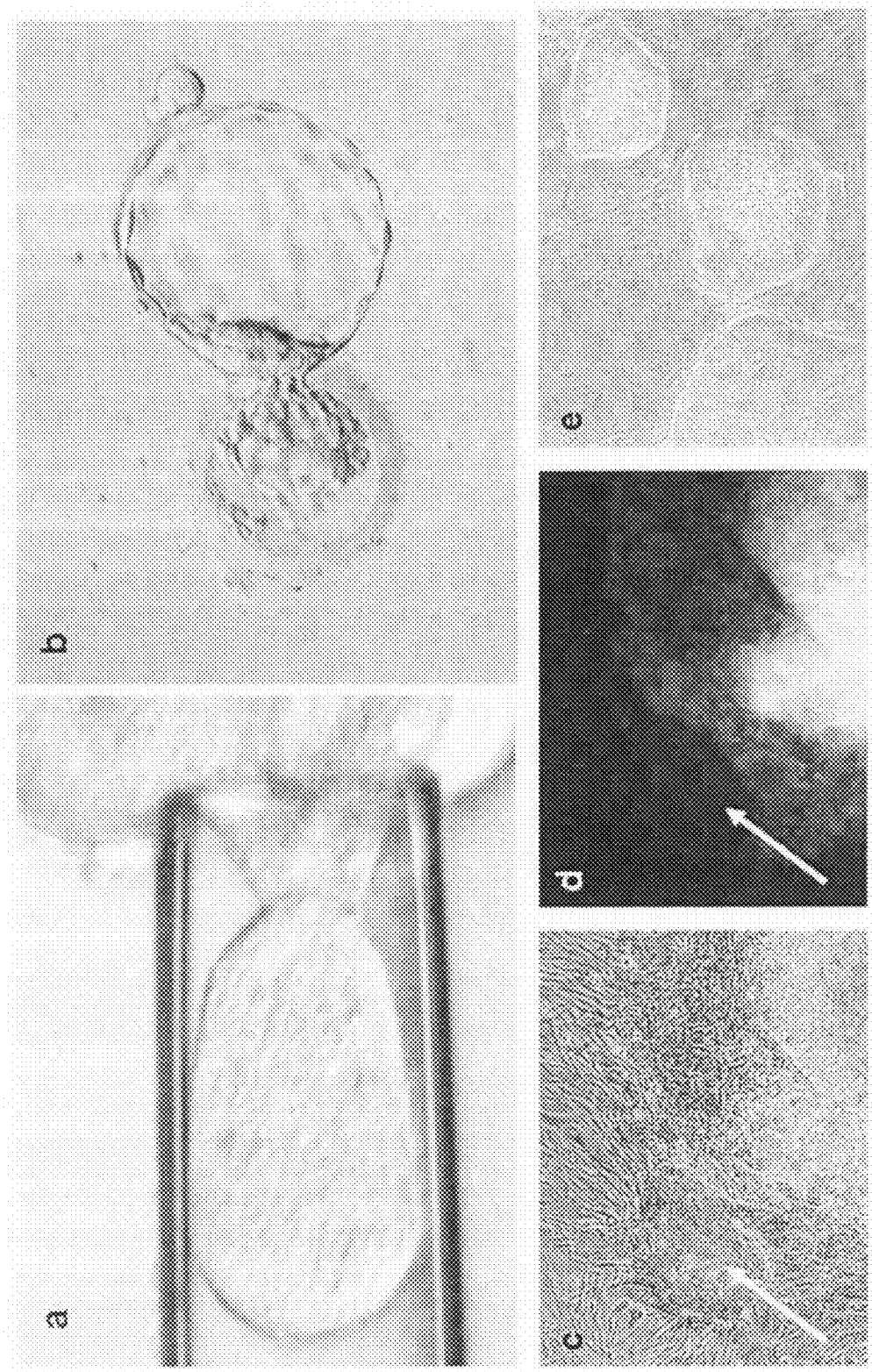
FIG. 2(a) shows a biopsy of a single blastomere; 2(b) shows the development of a blastomere-biopsied embryo into a hatching blastocyst; 2(c) and (d) shows blastomere-derived outgrowth (arrows) close to a colony of GFP-positive hES cells; 2(e) shows the morphology of blastomere-derived hES cell colonies.

Previous attempts to induce isolated human blastomeres to proliferate into pluripotent embryonic stem cells have failed (Geber S. et al., *Hum. Reprod.* 10:1492-1496 (1995)). The present invention is based, in part, on the discovery that stem cells can be generated from embryos without affecting viability of the embryo using novel methods disclosed herein. In one embodiment, these methods utilize in vitro techniques related to those currently used in pre-implantation genetic diagnosis (PGD) to isolate single blastomeres from embryos without destroying the embryos or otherwise significantly altering their viability. As demonstrated herein, pluripotent human embryonic stem (hES) cells and cell lines can be generated from a single blastomere removed from an embryo without interfering with the embryo's normal development to birth.

The methods described herein have numerous important uses that will advance the field of stem cell research and developmental biology. ES cells, ES cell lines, TS cells and cell lines, and cells differentiated therefrom can be used to study basic developmental biology, and can be used therapeutically in the treatment of numerous diseases and conditions. Additionally, these cells can be used in screening assays to identify factors and conditions that can be used to modulate the growth, differentiation, survival, or migration of these cells. Identified agents can be used to regulate cell behavior in vitro and in vivo, and may form the basis of cellular or cell-free therapies.

In order that the invention herein described may be fully understood, the following detailed description is set forth.

Unless defined otherwise, all technical and scientific terms used herein have the same meaning as those commonly understood by one of ordinary skill in the art to which this invention belongs. Although methods and materials similar or equivalent to those described herein can be used in the invention or testing of the present invention, suitable methods and materials are described below. The materials, methods and examples are illustrative only, and are not intended to be limiting.

All publications, patents, patent publications and applications and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

The articles "a" and "an" are used herein to refer to one or to more than one (i.e., to at least one) of the grammatical object of the article. By way of example, "an element" means one element or more than one element.

The term "blastomere" is used throughout to refer to at least one blastomere (e.g., 1, 2, 3, 4, etc) obtained from an embryo. The term "cluster of two or more blastomeres" is used interchangeably with "blastomere-derived outgrowths" to refer to the cells generated during the in vitro culture of a blastomere. For example, after a blastomere is obtained from an embryo and initially cultured, it generally divides at least once to produce a cluster of two or more blastomeres (also known as a blastomere-derived outgrowth). The cluster can be further cultured with embryonic or fetal cells. Ultimately, the blastomere-derived outgrowths will continue to divide. From these structures, ES cells, TS cells, and partially differentiated cell types will develop over the course of the culture method.

As summarized above, the present invention provides methods for deriving ES cells, ES cell lines, and differentiated cell types from single blastomeres of an early stage embryo without necessarily destroying the embryo. Various features of the method a described in detail below. All of the combinations of the various aspects and embodiments of the invention detailed above and below are contemplated.

Removal of the Blastomere

The blastomere may be removed from an embryo at various developmental stages prior to implantation including but not limited to: before compaction of the morula, during compaction of the morula, right after compaction of the morula, before formation of the blastocoel or during the blastocyst stage. In certain embodiments, a blastomere (one blastomere, two blastomeres, or more than two blastomeres) is removed from an embryo at the 4-16 cell stage, or at the 4-10 cell stage, or at the 4-8 cell stage.

In one embodiment the invention provides methods for biopsy of a blastocyst which will produce embryonic stem cells, and the remainder of the blastocyst is implanted and results in a pregnancy and later in a live birth. In an example of this: the zona pellucida is removed from the blastocyst by any means known to those of ordinary skill in the art and then the blastocyst is biopsied.

In another embodiment the controversies associated with the derivation of human ES cells are circumvented by using a technique similar to that used in preimplantation genetic diagnosis (PGD) where a single blastomere is removed from the embryo. In one embodiment, the single blastomere is removed before the compaction of the morula. The biopsied blastomere could be allowed to undergo cell division and one progeny cell is used for genetic testing and the remaining cells are used to generate human stem cells. The biopsied embryo may also be implanted at the blastocyst stage or frozen for implantation at a later time.

In certain embodiments, biopsy (e.g., removal of a blastomere from an embryo) consists of two stages. The first is to make a hole in, or in some instances fully remove, the zone pellucida that surrounds the embryo. Once the hole is made, the cells (preferably one or two) may then be removed from the human embryo. In certain preferred embodiments, the method involves removing or generating an extraction hole in the zona pellucida, and can be carried out by one or more techniques such as physical manipulation, chemical treatment and enzymatic digestion. Exemplary techniques that could be used include:

Partial zone dissection (PZD:): partial dissection of the zona pellucida, using a micro-pipette;

Zona drilling: chemical opening of the zona pellucida zone through partial digestion with Tyrode acid;

Zona drilling: enzymatic opening of the zona pellucida zone through partial digestion with pronase or other protease;

zona pellucida thinning: thinning of the zona pellucida with Tyrode acid or laser;

Point-like opening of the zona pellucida with laser;

Point-like mechanical opening of the zona pellucida with Piezo micro-manipulator.

To briefly illustrate one embodiment, the procedure is performed on 8-10 cell stage embryos. The embryo is placed in a drop of biopsy medium under mineral oil by holding it with a holding pipette. The zona pellucida is locally digested, by releasing acidified Tyrode's solution (Sigma, St. Louis, Mo. 63178) through an assistant hatching pipette. Once the hole is made, cells (blastomeres) could be aspirated through the hole.

To illustrate another embodiment, the zona pellucida of the blastocyst may be at least partially digested by treatment with one or more enzymes or mixture of enzymes such as pronase. A brief pronase (Sigma) treatment of blastocysts with an intact zona pellucida results in the removal of the zona. Other types of proteases with the same or similar protease activity as pronase may also be used.

Single blastomeres may also be obtained by disaggregating zona-denuded embryos in $Ca^{++}/Mg^{++}$ free PBS.

This invention also provides a novel and more efficient method of isolating single blastomeres. The embryo is immobilized and the immobilized embryo is then tapped until a single blastomere is released from the blastocyst. This method is not limited to human embryos and can be performed on embryos of other species including, without limitation, non-human embryos such as non-human mammals, mice, rabbits, pigs, cows, sheep, dogs and primates.

The embryo can be immobilized by any means known to those of skill in the art. In one embodiment, the embryo is immobilized using a micropipette and the micropipette holder is tapped to isolate the blastomere. In another embodiment, the embryo is cultured in medium that is calcium and magnesium free. The embryo may be from the 2-cell stage to the 16 cell stage. In one embodiment, the embryo is from the 4 cell stage to the 10 cell stage. In another embodiment the embryo is a 6-8 cell stage embryo. In yet another embodiment, the embryo is an 8-10 cell stage embryo. In certain embodiments, tapping involves generating an amount of force sufficient to remove at least one blastomere without substantially decreasing the viability of the remainder of the embryo. Maintenance of viability can be shown, for example, by culturing the remaining embryo for at least one day and confirming that the remaining embryo can continue to divide in culture.

Any of the foregoing methods can be used to obtain a blastomere (one blastomere or more than one blastomere) from an embryo. A particular method can be used alone or in combination with another method to facilitate removal of a blastomere.

In certain embodiments, the embryo is a mammalian embryo. In certain embodiments, the mammalian embryo is a human embryo. Exemplary mammals include, but are not limited to, mice, rats, rabbits, cows, dogs, cats, sheep, hamsters, pigs, non-human primates, and humans.

In certain embodiments of any of the foregoing, a blastomere is removed from an embryo without destroying the remainder of the embryo. The remaining embryo (the embryo minus the removed blastomere) can be cultured and/or cryopreserved. In certain embodiments, the remaining embryo is cultured for a time sufficient to confirm that the remaining embryo can continue to divide (e.g., is still viable), and then once viability is confirmed, the remaining embryo is cryopreserved. In certain other embodiments, the remaining embryo is immediately cryopreserved.

In certain other embodiments, multiple blastomeres are removed from a single embryo and the embryo is destroyed during or subsequent to the removal of multiple blastomeres. Multiple blastomeres can be used together in one experiment, for example, by aggregating multiple blastomeres during the initial blastomere culture. Alternatively, multiple blastomeres can be used in separate experiments in an effort to maximize the number of lines or cell types than can be generated from a single embryo.

Embryos from which a blastomere is obtained can be generated by sexual or asexual methods. In certain embodiments, the embryo is produced by fertilization of an egg with a sperm. In certain other embodiments, the embryo is produced by somatic cell nuclear transfer, parthenogenesis, androgenesis, or other asexual techniques. Note that embryos derived from asexual techniques may not look identical to embryos generated by fertilization. However, despite any differences in appearance, the term embryo is intended to encompass the products of asexual reproduction and the products of fertilization or other means of sexual reproduction.

Culturing the Blastomere and Production of ES Cells

Once removed from the embryo, the isolated blastomere(s) can be initially cultured in any type of medium, e.g., embryo medium such as Quinn's cleavage medium (Cooper Surgical Inc. Cat #ART1529). Any medium that supports growth of an embryo can be used, including, without limitation, any commercial formulations. As used herein, the term "embryo medium" is used to refer to a medium that promotes survival of blastomeres (especially human blastomeres) in culture. In certain embodiments, the embryo medium is a medium containing less than 5 mM glucose. In certain embodiments, the embryo medium is a medium that has an osmolarity of less that 310 mosm. In certain other embodiments, the embryo medium is a medium that contains less than 5 mM glucose and has an osmolarity of less than 310 mosm. In certain embodiments, the medium used to initially culture blastomeres has an osmolarity of less than 300 mosm, less than 280 mosm, or less than 260 mosm, and optionally contains less than 5 mM glucose. In certain embodiments, the medium used to initially culture blastomeres has an osmolarity about 260-280 mosm, and optionally contains less than 5 mM glucose. Note that regardless of the osmolarity and particular concentration of glucose in the medium used to initially culture the blastomeres, the medium may also be supplemented with antibiotics, minerals, amino acids, and other factors typically found in commercial media formulations.

The blastomeres may not initially grow well in standard ES cell medium. However, as described in detail herein, once the blastomeres have been cultured in the presence of certain embryonic or fetal cells and/or allowed to divide one or more times, the cluster of blastomeres can optionally be cultured in ES cell medium, or may be slowly transferred from embryo medium to ES cell medium by gradually replacing the medium. As used herein, the term "ES cell medium" is used to refer to a medium that promotes maintenance of ES cells in culture and can be used to culture clusters of blastomeres as they continue to divide and produce ES cells, ED cells, etc. Such a medium is at least somewhat optimized for ES cells. In certain embodiments, the ES cell medium contains at least 5 mM glucose (relatively high glucose). In certain other embodiments, the ES cell medium has an osmolarity of at least 310 mosm. In certain other embodiments, the medium contains at least 5 mM glucose and has an osmolarity of at least 310 mosm. In certain embodiments, this medium has an osmolarity of at least 320 mosm, or at least 330 mosm, and optionally contains at least 5 mM glucose. In certain embodiments, this medium has an osmolarity of about 310-340 mosm, and optionally contains at least 5 mM glucose. ES cell medium may also be supplemented with factors known in the art to promote the growth of ES cells, and the medium may contain antibiotics, minerals, amino acids, and other factors typically found in commercial media formulations.

In certain embodiments, a blastomere is obtained from a human or other mammalian embryo and cultured in embryo medium. Preferably, a blastomere is cultured in embryo medium for at least one day or until the blastomere divides at least once. However, a blastomere may be cultured in embryo medium for more than 1 day (at least 2, 3, 4 days, etc.) and/or the blastomere may be cultured in contact with embryonic or fetal cells before dividing to produce a cluster of blastomere. When cultured in embryo medium, the blastomere may divide one or more times or produce a cluster of two or more blastomeres. Further culturing of the cluster of blastomeres includes culturing the blastomere along with its progeny. In certain embodiments, the blastomere divides and the progeny are cultured as an aggregate.

In one embodiment, the blastomere can be cultured in a microdrop. Each microdrop can contain a single blastomere or multiple blastomeres. After about at least 1 day, at least 2-3 days, or at least 4 days, the cultured blastomeres may divide and form vesicles or aggregates. The benefit of culturing the blastomere prior to direct or indirect contact with the embryonic cells is to prevent the embryonic cells from overgrowing the blastomere.

After a blastomere is initially cultured to generate a cluster of two or more blastomeres, the cultured cluster of two or more blastomeres is contacted directly or indirectly with embryonic or fetal cells, or alternatively with a medium that promotes further maturation of the blastomeres in the absence of embryonic or fetal cells. Such medium includes medium conditioned with embryonic or fetal cells (conditioned medium) or medium supplemented with growth factors or cytokines that promote maturation of the blastomeres. In certain embodiments, the medium is supplemented with ACTH (adrenocorticotropic hormone).

For embodiments in which direct or indirect culture with embryonic or fetal cells is used, the embryonic or fetal cells may be derived from, for example, a mammal. In certain embodiments, the embryonic or fetal cells are mouse or human cells. Exemplary embryonic or fetal cells include, but are not limited to, embryonic stem (ES) cells (whether derived from blastocysts, blastomeres, or by other methods, and whether derived using somatic cell nuclear transfer or other asexual reproduction), embryonic germ cells, embryonic carcinoma cells, placental cells, trophoblasts/trophectoderm cells, trophoblast stem cells, primordial germ cells embryonic germ cells, amniotic fluid cells, amniotic stem cells, placental cells, placental stem cells, and umbilical cord cells. In certain embodiments in which blastomeres are directly or indirectly contacted with embryonic or fetal cells, the medium in which the blastomeres are cultured is further supplemented with ACTH or other growth factors or cytokines that promote maturation of the blastomeres.

When used, the embryonic or fetal cells, may be grown in the presence or absence of a feeder layer of cells. Feeder cells may be used to help maintain the embryonic or fetal cells and to prevent their differentiation. The specific feeder cell may be chosen based on the particular embryonic or fetal cell used. Exemplary feeder cells include, but are not limited to, fibroblast feeder cells. Such fibroblast feeder cells may be derived from the same species as the embryonic or fetal cells or they may be derived from a different species. Similarly, the feeder cells and the embryonic or fetal cells may be derived from the same species as the blastomere or from a different species. In certain embodiments, the feeder cells are irradiated or otherwise treated to prevent overgrowth relative to the embryonic or fetal cells. Exemplary feeder cells include, but are not limited to, mouse embryonic fibroblasts (MEF cells), human embryonic fibroblasts, human foreskin fibroblasts, human skin fibroblasts, human endometrial fibroblasts, human oviductal fibroblasts, and placental cells. Similar cell types derived from other animals (mammals, chickens, etc) are also contemplated.

In one embodiment, the feeder and/or embryonic cells are human cells that are autologous cells derived from the same embryo as the blastomere.

The embryonic or fetal cells are grown in ES cell medium or any medium that supports growth of the embryonic or fetal cells, e.g., Knockout DMEM (Invitrogen Cat # 10829-018). Exemplary embryonic or fetal cells include, but are not limited to, embryonic stem cells, such as from already established lines, embryo carcinoma cells, murine embryonic fibroblasts, other embryo-like cells, cells of embryonic origin or cells derived from embryos, many of which are known in the art and available from the American Type Culture Collection, Manassas, Va. 20110-2209, USA, and other sources.

The embryonic or fetal cells may be added directly to the cultured blastomeres or may be grown in close proximity to, but not in direct contact with, the cultured blastomere(s). Various direct and indirect co-culture systems are possible to facilitate providing the cultured blastomeres with factors or signals from the embryonic or fetal cells. As used herein, "contacting the cultured cluster of two or more blastomeres" refers to any method of direct or indirect contact or co-culture.

In certain embodiments, contacting the cluster of two or more blastomere comprises aggregating blastomere clusters with embryonic or fetal cells. In certain other embodiments, contacting comprises co-culturing the cluster of two or mores blastomeres so that the cells are in direct contact with the embryonic or fetal cells but are not aggregated to them. In other embodiments, contacting comprises co-culturing the cluster of two or more blastomeres with the embryonic or fetal cells so that the cells are in indirect contact, for example, maintained in the same culture vessel but without direct contact of the cells or maintained as contiguous microdrops.

In certain embodiments, the method comprises the step of directly or indirectly contacting the cultured cluster of two or more blastomere(s) with embryonic or fetal cells, with the proviso that the contacting is not carried out by aggregating the cultured blastomere with embryonic cells as described in Chung et al., *Nature* (2006) 439:216-9. Alternatively, the culture of blastomere(s) and the culture of embryonic or fetal cells are indirectly connected or merged. This can be achieved by any method known in the art including, for example, dragging a manipulation pipette between two drops under light mineral oil such as Cooper Surgical ACT# ART4008, paraffin oil or Squibb's oil. The connections can be made by using a glass capillary or similar device. Such indirect connections between the cultured blastomere and the embryonic cells allows gradual mixing of the embryo medium (in which the blastomere is cultured) and the ES cell medium (in which the human embryonic cells are grown). In another embodiment, the blastomere(s) may be co-cultured with the remaining embryo. For example, the blastomere is co-cultured with the remaining embryo in a microdroplet culture system or other culture system known in the art, which does not permit cell-cell contact but could permit cell-secreted factor and/or cell-matrix contact. The volume of the microdrop may be reduced, e.g., from 50 microliters to about 5 microliters to intensify the signal. In another embodiment the embryonic cells may be from a species other than human, e.g., non-human primate or mouse.

In certain embodiments, the particular media formulations used to culture a blastomere, a cluster of two or more blastomeres, and embryonic or fetal cells may vary slightly depending on the species. Additionally, whether initial blastomere culture benefits from a media formulation different from that used to culture the clusters of blastomeres or the embryonic cells may also vary slightly depending on the species.

In certain embodiments, the medium used to separately culture a blastomere and the medium used to culture embryonic or fetal cells is not necessarily the same. In embodiments for which the media differ, there may be a period where the blastomere or cluster of blastomeres is being initially exposed to a medium that differs from the medium in which the blastomere was initially cultured (e.g., the cells will be slowly exposed to the medium in which the embryonic or fetal cells were cultured). In such embodiments, the cluster of two or more blastomeres, which has now divided multiple times to give rise to a cluster of cells and cell outgrowths, can gradually be transferred (for example by exchanging the medium) and cultured in medium having the properties of ES cell medium.

After about 3-4 days, the blastomere(s) exhibit properties of ES cells. Specifically, as the cells continue to divide and the blastomere progeny cluster, various cell types emerge and can be identified phenotypically. Amongst the emerging cell types are trophectoderm-like cells, ES cells, and partially or terminally differentiated ED cells. As such, these methods can be used to produce ES cells, TS or other trophectoderm cells, or ED cells. While not wishing to be bound by any particular theory, it is believed that over a period of days or weeks the cultured blastomeres exhibit ES cell growth perhaps as a result of factors secreted by the embryonic or fetal cells or by the extracellular matrix. Further, the dividing cluster of blastomere progeny resemble, in some respects, the changes observed during development of the preimplantation blastocyst. As such, the cell types emerging in these cultures recapitulate to some extent the cell types observed when whole blastocysts or ICMs are plated.

In certain embodiments, the blastomere culture conditions may include contacting the cells with factors that can inhibit or otherwise potentiate the differentiation of the cells, e.g., prevent the differentiation of the cells into non-ES cells, trophectoderm or other cell types. Such conditions can include contacting the cultured cells with heparin or introducing Oct-4 into the cells (such as by including Oct-4 in the media) or activating endogenous Oct-4 in the cells. In yet another embodiment, expression of cdx-2 is prevented by any means known in the art including, without limitation, introducing CDX-2 RNAi into blastomeres, thereby inhibiting differentiation of the blastomere into TS cells.

As detailed above, the invention provides methodologies for producing ES cells, ED cells, and TS cells from a blastomere obtained from an embryo. This approach can be used to generate ES cells, ED cell, and TS cells, as well as cell line without necessarily destroying the embryo from which the blastomere is obtained.

Culturing the Blastomere and Production of ED Cells

In the past, long-term culture of inner cell mass cells was used to produce embryonic stem cell lines. Subsequently, the embryonic stem cells were cultured and conditionally genetically-modified, and induced to differentiate in order to produce cells for therapy. U.S. patent application Ser. No. 11/025,893 (published as US 2005/0265976A1), incorporated herein in its entirety, describes a method of producing differentiated progenitor cells from inner cell mass cells or morula-derived cells by directly inducing the differentiation of those cells without producing an embryonic stem cell line and the use of said differentiated cells, tissues, and organs in transplantation therapy. Because these cells are derived from the cells of the embryo but not from an ES cell line, we designate such cells as embryo-derived (ED) cells. Blastomere-derived ED cells have broader differentiation potential than human ES cells produced using methods known in the art because the ED cells can be readily differentiated into germ-line cells using techniques known in the art, e.g. using methods to differentiate murine ES cell lines into germ-line cells. In contrast, human ES cell lines derived from inner mass cells are not expected to be capable of differentiation into germ-line cells. This phenomenon has been observed in ES cells derived from inner mass cells in animal such as pigs, cows, chickens and rats and is likely due to the fact that germ-line is one of the first cell lineages to branch out in differentiation.

In some of the methods of the present invention, blastomeres from embryos with at least two cells, and before the embryo enters the stage of development of a compacting morula are induced to directly differentiate into differentiated progenitor cells which are then used for cell therapy and for the generation of cells, tissues, and organs for transplantation. If desired, genetic modifications can be introduced, for example, into somatic cells prior to nuclear transfer to produce a morula or blastocyst or into somatic cells prior to the reprogramming of said somatic cell into undifferentiated cells through the juxtaposition of the DNA of said somatic cell with factors capable of reprogramming said somatic cells or into ES cell lines made using these methods. See U.S. patent application Ser. No. 10/831,599 published as US 2004199935, PCT/US06/30632 filed Aug. 3, 2006, and U.S. Provisional Patent Application Nos. 60/705,625, 60/729,173 and 60/818,813, the disclosure of which are incorporated herein by reference in their entirety. Thus, the differentiated progenitor cells of the present invention do not possess the pluripotency of an embryonic stem cell, or an embryonic germ cell, and are, in essence, tissue-specific partially or fully differentiated cells. These differentiated progenitor cells may give rise to cells from any of three embryonic germ layers, i.e., endoderm, mesoderm, and ectoderm. For example, the differentiated progenitor cells may differentiate into bone, cartilage, smooth muscle, dermis with a prenatal pattern of gene expression and capable of promoting scarless wound repair, and hematopoietic or hemangioblast cells (mesoderm), definitive endoderm, liver, primitive gut, pancreatic beta cells, and respiratory epithelium (endoderm); or neurons, glial cells, hair follicles, or eye cells including retinal neurons and retinal pigment epithelium.

Furthermore, it is not necessary for the differentiated progenitor cells of the present invention to express the catalytic component of telomerase (TERT) and be immortal, or that the progenitor cells express cell surface markers found on embryonic stem cells such as the cell surface markers characteristic of primate embryonic stem cells: positive for SSEA-3, SSEA-4, TRA-1-60, TRA-1-81, alkaline phosphatase activity, and negative for SSEA-1. Moreover, the differentiated progenitor cells of the present invention are distinct from embryoid bodies, i.e., embryoid bodies are derived from embryonic stem cells whereas the differentiated stem cells of the present invention are derived from blastomeres.

Preferably, the differentiated cells of the present invention are produced by culturing blastomere-derived cells in the absence of embryonic stem cells. Growth of undifferentiated embryonic stem cells can be prevented, for example, by culturing blastomeres in the presence of differentiation-inducing agents or by introducing genetic modifications into the cells such that the growth of embryonic stem cells is prevented.

Any vertebrate embryo may be used as a source of blastomeres or cells equivalent in development to a mammalian blastomere. Human blastomeres, in particular, have important utility in the generation of human cell-based therapies. The original embryo may have been produced by in vitro-fertilization, derived by fertilization within the reproductive tract by normal sexual reproduction, artificial insemination, or gamete intrafallopian transfer (GIFT), and subsequently retrieved, derived by somatic cell nuclear transfer.

Differentiation

Methods for isolating blastomeres have already been described herein. Isolated blastomeres can be induced directly or via ES cells or cell lines to differentiate in the presence of differentiation-inducing conditions including various combinations of growth factors, sera, hormones, extracellular matrices useful in making the particular desired differentiated cell type as known in the art (see Table 2 for list of exemplary molecules), or as disclosed in the pending applications PCT/US2006/013573 filed Apr. 11, 2006, U.S. Application No. 60/835,779, filed Aug. 3, 2006, 60/792,224 filed Apr. 14, 2006, 60/801,993 filed May 19, 2006, PCT/US2006/013519 filed Apr. 11, 2006, U.S. application Ser. No. 11/025,893 (published as US 20050265976), WO2005/070011 published Aug. 4, 2005, and WO 2006/080952 published Aug. 3, 2006, the disclosure of which are incorporated herein by reference. For example, blastomeres or ES cells may be cultured on various inducer cell types such as those isolated as single cell-derived populations of cells, or on particular extracellular matrix components and other differentiation-inducing factors such as factors or combinations of factors shown in Table 2 below.

TABLE 2

| Culture Variables |
|---|
| EGF Ligands |
| 1) Amphiregulin |
| 2) Betacellulin |
| 3) EGF |
| 4) Epigen |
| 5) Epiregulin |
| 6) HB-EGF |
| 7) Neuregulin-3 |
| 8) NRG1 isoform GGF2 |
| 9) NRG1 Isoform SMDF |
| 10) NRG1-alpha/HRG1-alpha |
| 11) TGF-alpha |
| 12) TMEFF1/Tomoregulin-1 |
| 13) TMEFF2 |
| 14) EGF Ligands pooled (1-13 above) |
| EGF R/ErbB Receptor Family |
| 15) EGF Receptor |
| 16) ErbB2 |
| 17) ErbB3 |
| 18) ErbB4 |
| 19) EGF/ErbB Receptors pooled (15-18 above) |
| FGF Ligands |
| 20) FGF acidic |
| 21) FGF basic |
| 22) FGF-3 |
| 23) FGF-4 |
| 24) FGF-5 |
| 25) FGF-6 |
| 26) KGF/FGF-7 |
| 27) FGF-8 |
| 28) FGF-9 |
| 29) FGF-10 |
| 30) FGF-11 |
| 31) FGF-12 |
| 32) FGF-13 |
| 33) FGF-14 |

TABLE 2-continued

Culture Variables

34) FGF-15
35) FGF-16
36) FGF-17
37) FGF-18
38) FGF-19
39) FGF-20
40) FGF-21
41) FGF-22
42) FGF-23
43) FGF Ligands pooled (20-38 above)
FGF Receptors 40) FGF R1
41) FGF R2
42) FGF R3
43) FGF R4
44) FGF R5
45) FGF Receptors pooled (40-44 above)
FGF Regulators 46) FGF-BP
Hedgehogs 47) Desert Hedgehog
48) Sonic Hedgehog
49) Indian Hedgehog
50) Hedgehogs pooled (47-49 above)
Hedgehog Regulators 51) Gas1
52) Hip
53) Hedgehog Regulators pooled (51-52 above)
IGF Ligands 54) IGF-I
55) IGF-II
56) IGF Ligands pooled (54-55 above)
IGF-I Receptor (CD221)

57) IGF-I R
GF Binding Protein (IGFBP) Family

58) ALS
59) IGFBP-4
60) CTGF/CCN2
61) IGFBP-5
62) Endocan
63) IGFBP-6
64) IGFBP-1
65) IGFBP-rp1/IGFBP-7
66) IGFBP-2
67) NOV/CCN3
68) IGFBP-3
69) GF Binding Protein Family pooled (58-68 above)
Receptor Tyrosine Kinases 70) Axl
71) C1q R1/CD93
72) DDR1
73) Flt-3
74) DDR2
75) HGF R
76) Dtk
77) IGF-II R
78) Eph
79) Insulin R/CD220
80) EphA1
81) M-CSF R
82) EphA2
83) Mer
84) EphA3
85) MSP R/Ron
86) EphA4
87) MuSK 88) EphA5
89) PDGF R alpha
90) EphA6
91) PDGF R beta
92) EphA7
93) Ret
94) EphA8
95) ROR1
96) EphB1
97) ROR2
98) EphB2
99) SCF R/c-kit
100) EphB3
101) Tie-1
102) EphB4
103) Tie-2
104) EphB6
105) TrkA
106) TrkB
107) TrkC
108) VEGF R1/Flt-1
109) VEGF R2/Flk-1
110) VEGF R3/Flt-4
111) Receptor Tyrosine Kinases pooled (70-110 above)
Proteoglycans 112) Aggrecan
113) Lumican
114) Biglycan
115) Mimecan
116) Decorin
117) NG2/MCSP
118) Endocan
119) Osteoadherin
120) Endorepellin
121) Syndecan-1/CD138
122) Glypican 2
123) Syndecan-3
124) Glypican 3
125) Testican 1/SPOCK1
126) Glypican 5
127) Testican 2/SPOCK2
128) Glypican 6
129) Testican 3/SPOCK3
130) Heparan sulfate proteoglycan
131) Heparin
132) Chondroitin sulfate proteoglycan
133) Hyaluronic acid
134) Dermatan sulfate proteoglycan
Proteoglycan Regulators 135) Arylsulfatase A/ARSA
136) HAPLN1
137) Exostosin-like 2
138) HS6ST2
139) Exostosin-like 3
140) IDS
141) Proteoglycan Regulators pooled (135-140 above)
SCF, Flt-3 Ligand & M-CSF 142) Flt-3
143) M-CSF R
144) Flt-3 Ligand
145) SCF
146) M-CSF
147) SCF R/c-kit
148) Pooled factors (142-147 above)
Activins 149) Activin A
150) Activin B
151) Activin AB
152) Activin C
153) Pooled Activins (149-152 above)

TABLE 2-continued

Culture Variables

BMPs (Bone Morphogenetic Proteins)

154) BMP-2
155) BMP-3
156) BMP-3b/GDF-10
157) BMP-4
158) BMP-5
159) BMP-6
160) BMP-7
161) BMP-8
162) Decapentaplegic
163) Pooled BMPs (154-162 above)

GDFs (Growth Differentiation Factors)

164) GDF-1
165) GDF-2
166) GDF-3
167) GDF-4
168) GDF-5
169) GDF-6
170) GDF-7
171) GDF-8
172) GDF-9
173) GDF-10
174) GDF-11
175) GDF-12
176) GDF-13
177) GDF-14
178) GDF-15
179) GDFs pooled (164-178 above)

GDNF Family Ligands

180) Artemin
181) Neurturin
182) GDNF
183) Persephin
184) GDNF Ligands pooled (180-183 above)

TGF-beta

185) TGF-beta
186) TGF-beta 1
187) TGF-beta 1.2
188) TGF-beta 2
189) TGF-beta 3
190) TGF-beta 4
191) TGF-beta 5
192) LAP (TGF-beta 1)
193) Latent TGF-beta 1
194) TGF-beta pooled (185-193 above)

Other TGF-beta Superfamily Ligands

195) Lefty
196) Nodal
197) MIS/AMH
198) Other TGF-beta Ligands pooled (195-197 above)

TGF-beta Superfamily Receptors

199) Activin RIA/ALK-2
200) GFR alpha-1
201) Activin RIB/ALK-4
202) GFR alpha-2
203) Activin RIIA
204) GFR alpha-3
205) Activin RIIB
206) GFR alpha-4
207) ALK-1
208) MIS RII
209) ALK-7
210) Ret
211) BMPR-IA/ALK-3
212) TGF-beta RI/ALK-5
213) BMPR-IB/ALK-6
214) TGF-beta RII
215) BMPR-II
216) TGF-beta RIIb
217) Endoglin/CD105
218) TGF-beta RIII
219) TGF-beta family receptors pooled (199-218 above)

TGF-beta Superfamily Modulators

220) Amnionless
221) GASP-2/WFIKKN
222) BAMBI/NMA
223) Gremlin
224) Caronte
225) NCAM-1/CD56
226) Cerberus 1
227) Noggin
228) Chordin
229) PRDC
230) Chordin-Like 1
231) Chordin-Like 2
232) Smad1
233) Smad4
234) Smad5
235) Smad7
236) Smad8
237) CRIM1
238) Cripto
239) Crossveinless-2
240) Cryptic
241) SOST
242) DAN
243) Latent TGF-beta bp1
244) TMEFF1/Tomoregulin-1
245) FLRG
246) TMEFF2
247) Follistatin
248) TSG
249) Follistatin-like 1
250) Vasorin
251) GASP-1/WFIKKNRP
252) TGF Modulators pooled (220-251 above)

VEGF/PDGF Family

253) Neuropilin-1
254) PlGF
255) PlGF-2
256) Neuropilin-2
257) PDGF
258) VEGF R1/Flt-1
259) PDGF R alpha
260) VEGF R2/Flk-1
261) PDGF R beta
262) VEGF R3/Flt-4
263) PDGF-A
264) VEGF
265) PDGF-B
266) VEGF-B
267) PDGF-C
268) VEGF-C
269) PDGF-D
270) VEGF-D
271) PDGF-AB
272) VEGF/PDGF Family pooled (253-271 above)

Dickkopf Proteins & Wnt Inhibitors

273) Dkk-1
274) Dkk-2
275) Dkk-3
276) Dkk-4
277) Soggy-1
278) WIF-1
279) Pooled factors (273-278 above)

Frizzled & Related Proteins

280) Frizzled-1

TABLE 2-continued

Culture Variables

281) Frizzled-2
282) Frizzled-3
283) Frizzled-4
284) Frizzled-5
285) Frizzled-6
286) Frizzled-7
287) Frizzled-8
288) Frizzled-9
289) sFRP-1
290) sFRP-2
291) sFRP-3
292) sFRP-4
293) MFRP
294) Factors pooled (280-293 above)

Wnt Ligands

295) Wnt-1
296) Wnt-2
297) Wnt-3
298) Wnt-3a
299) Wnt-4
300) Wnt-5
301) Wnt-5a
302) Wnt-6
303) Wnt-7
304) Wnt-8
305) Wnt-8a
306) Wnt-9
307) Wnt-10a
308) Wnt-10b
309) Wnt-11
310 Wnt Ligands pooled (295-309 above)

Other Wnt-related Molecules 311) beta-Catenin
312) LRP-6
313) GSK-3
314) ROR1
315) Kremen-1
316) ROR2
317) Kremen-2
318) WISP-1/CCN4
319) LRP-1
320) Pooled factors (311-319 above)

Other Growth Factors

321) CTGF/CCN2
322) NOV/CCN3
323) EG-VEGF/PK1
324) Osteocrin
325) Hepassocin
326) PD-ECGF
327) HGF
328) Progranulin
329) beta-NGF
330) Thrombopoietin
331) Pooled factors (321-330 above)

Steroid Hormones 332) 17beta-Estradiol
333) Testosterone
334) Cortisone
335) Dexamethasone Extracellular/Memrane Proteins 336) Plasma Fibronectin
337) Tissue Fibronectin
338) Fibronectin fragments
339) Collagen Type I (gelatin)
340) Collagen Type II
341) Collagen Type III
342) Tenascin
343) Matrix Metalloproteinase 1
344) Matrix Metalloproteinase 2
345) Matrix Metalloproteinase 3
346) Matrix Metalloproteinase 4

TABLE 2-continued

Culture Variables

347) Matrix Metalloproteinase 5
348) Matrix Metalloproteinase 6
349) Matrix Metalloproteinase 7
350) Matrix Metalloproteinase 8
351) Matrix Metalloproteinase 9
352) Matrix Metalloproteinase 10
353) Matrix Metalloproteinase 11
354) Matrix Metalloproteinase 12
355) Matrix Metalloproteinase 13
356) ADAM-1
357) ADAM-2
358) ADAM-3
359) ADAM-4
360) ADAM-5
361) ADAM-6
362) ADAM-7
363) ADAM-8
364) ADAM-9
365) ADAM-10
366) ADAM-11
367) ADAM-12
368) ADAM-13
369) ADAM-14
370) ADAM-15
371) ADAM-16
372) ADAM-17
373) ADAM-18
374) ADAM-19
375) ADAM-20
376) ADAM-21
377) ADAM-22
378) ADAM-23
379) ADAM-24
380) ADAM-25
381) ADAM-26
382) ADAM-27
383) ADAM-28
384) ADAM-29
385) ADAM-30
386) ADAM-31
387) ADAM-32
388) ADAM-33
389) ADAMTS-1
390) ADAMTS-2
391) ADAMTS-3
392) ADAMTS-4
393) ADAMTS-5
394) ADAMTS-6
395) ADAMTS-7
396) ADAMTS-8
397) ADAMTS-9
398) ADAMTS-10
399) ADAMTS-11
400) ADAMTS-12
401) ADAMTS-13
402) ADAMTS-14
403) ADAMTS-15
404) ADAMTS-16
405) ADAMTS-17
406) ADAMTS-18
407) ADAMTS-19
408) ADAMTS-20
409) Arg-Gly-Asp
410) Arg-Gly-Asp-Ser
411) Arg-Gly-Asp-Ser-Pro-Ala-Ser-Ser-Lys-Pro
412) Arg-Gly-Glu-Ser
413) Arg-Phe-Asp-Ser
414) SPARC
415) Cys-Asp-Pro-Gly-Tyr-Ile-Gly-Ser-Arg
416) Cys-Ser-Arg-Ala-Arg-Lys-Gln-Ala-Ala-Ser-Ile-Lys-Val-Ser-Ala-Asp-Arg
417) Elastin
418) Tropelastin
419) Gly-Arg-Gly-Asp-Ser-Pro-Lys

TABLE 2-continued

Culture Variables

420) Gly-Arg-Gly-Asp-Thr-Pro
421) Laminin
422) Leu-Gly-Thr-Ile-Pro-Gly
423) Ser-Asp-Gly-Arg-Gly
424) Vitronectin
425) Superfibronectin
426) Thrombospondin
427) TIMP-1
428) TIMP-2
429) TIMP-3
430) TIMP-4
431) Fibromodulin
432) Flavoridin
433) Collagen IV
434) Collagen V
435) Collagen VI
436) Collagen VII
437) Collagen VIII
438) Collagen IX
439) Collagen X
440) Collagen XI
441) Collagen XII
442) Entactin
443) Fibrillin
444) Syndecan-1
445) Keratan sulfate proteoglycan Ambient Oxygen 446) 0.1-0.5% Oxygen
447) 0.5-1% Oxygen
448) 1-2% Oxygen
449) 2-5% Oxygen
450) 5-10% Oxygen
451) 10-20% Oxygen Animal Serum 452) 0.1% Bovine Serum
453) 0.5% Bovine Serum
454) 1.0% Bovine Serum
455) 5.0% Bovine Serum
456) 10% Bovine Serum
457) 20% Bovine Serum
458) 10% Horse Serum Interleukins 459) IL-1
460) IL-2
461) IL-3
462) IL-4
463) IL-5
464) IL-6
465) IL-7
466) IL-8
467) IL-9
468) IL-10
469) IL-11
470) IL-12
471) IL-13
472) IL-14
473) IL-15
474) IL-16
475) IL-17
476) IL-18

Proteases

477) MMP-1
478) MMP-2
479) MMP-3
480) MMP-4
481) MMP-5
482) MMP-6
483) MMP-7
484) MMP-8
485) MMP-9
486) MMP-10
487) MMP-11
488) MMP-12

TABLE 2-continued

Culture Variables

489) MMP-13
490) MMP-14
491) MMP-15
492) MMP-16
493) MMP-17
494) MMP-18
495) MMP-19
496) MMP-20
497) MMP-21
498) MMP-22
499) MMP-23
500) MMP-24
501) Cathepsin B
501) Cathepsin C
503) Cathepsin D
504) Cathepsin G
505) Cathepsin H
506) Cathepsin L
507) Trypsin
508) Pepsin
509) Elastase
510) Carboxypeptidase A
511) Carboxypeptidase B
512) Carboxypeptidase G
513) Carboxypeptidase P
514) Carboxypeptidase W
515) Carboxypeptidase Y
516) Chymotrypsin
517) Plasminogen
518) Plasmin
519) u-type Plasminogen activator
520) t-type Plasminogen activator
521) Plasminogen activator inhibitor-1
522) Carboxypeptidase Z Amino Acids 522) Alanine
523) Arginine
524) Asparagine
525) Aspartic acid
526) Cysteine
527) Glutamine
528) Glutamic acid
529) Glycine
530) Histidine
531) Isoleucine
532) Leucine
533) Lysine
534) Methionine
535) Phenylalanine
536) Proline
537) Serine
538) Threonine
539) Tryptophan
540) Tyrosine
541) Valine Prostaglandins 542) Prostaglandin A1
543) Prostaglandin A2
544) Prostaglandin B1
545) Prostaglandin B2
546) Prostaglandin D2
547) Prostaglandin E1
548) Prostaglandin E2
549) Prostaglandin F1alpha
550) Prostaglandin F2alpha
551) Prostaglandin H
552) Prostaglandin I2
553) Prostaglandin J2
554) 6-Keto-Prostaglandin F1a
555) 16,16-Dimethyl-Prostaglandin E2
556) 15d-Prostaglandin J2
557) Prostaglandins pooled (542-556 above)

TABLE 2-continued

Culture Variables

Retinoid receptor agonists/Antagonists

558) Methoprene Acid
559) All trans retinoic acid
560) 9-Cis Retinoic Acid
561) 13-Cis Retinoic Acid
562) Retinoid agonsts pooled (558-561 above)
563) Retinoid antagonists
564) Retinoic acid receptor isotype RARalpha
565) Retinoic acid receptor isotype RARbeta
566) Retinoic acid receptor isotype RARgamma
567) Retinoic X receptor isotype RXRalpha
568) Retinoic X receptor isotype RXRbeta
569) Retinoic X receptor isotype RARgamma Miscellaneous Inducers 570) Plant lectins
571) Bacterial lectins
572) forskolin
573) Phorbol myristate acetate
574) Poly-D-lysine
575) 1,25-dihydroxyvitamin D
576) Inhibin
577) Heregulin
578) Glycogen
579) Progesterone
580) IL-1
581) Serotonin
582) Fibronectin - 45 kDa Fragment
583) Fibronectin - 70 kDa Fragment
584) glucose
585) beta mercaptoethanol
586) heparinase
587) pituitary extract
588) chorionic gonadotropin
589) adrenocorticotropic hormone
590) thyroxin
591) Bombesin
592) Neuromedin B
593) Gastrin-Releasing Peptide
594) Epinephrine
595) Isoproterenol
596) Ethanol
597) DHEA
598) Nicotinic Acid
599) NADH
600) Oxytocin
601) Vasopressin
602) Vasotocin
603) Angiotensin I
604) Angiotensin II
605) Angiotensin I Converting Enzyme
606) Angiotensin I Converting Enzyme Inhibitor
607) Chondroitinase AB
608) Chondroitinase C
609) Brain natriuretic peptide
610) Calcitonin
611) Calcium ionophore I
612) Calcium ionophore II
613) Calcium ionophore III
614) Calcium ionophore IV
615) Bradykinin
616) Albumin
617) Plasmonate
618) LIF
619) PARP inhibitors
620) Lysophosphatidic acid
621) (R)-METHANANDAMIDE
622) 1,25-DIHYDROXYVITAMIN D3
623) 1,2-DIDECANOYL-GLYCEROL (10:0)
624) 1,2-DIOCTANOYL-SN-GLYCEROL
625) 1,2-DIOLEOYL-GLYCEROL (18:1)
626) 10-hydroxycamptothecin
627) 11,12-EPOXYEICOSATRIENOIC ACID
628) 12(R)-HETE
629) 12(S)-HETE
630) 12(S)-HPETE
631) 12-METHOXYDODECANOIC ACID
632) 13(S)-HODE
633) 13(S)-HPODE
634) 13,14-DIHYDRO-PGE1
635) 13-KETOOCTADECADIENOIC ACID
636) 14,15-EPOXYEICOSATRIENOIC ACID
637) 1400W
638) 15(S)-HETE
639) 15(S)-HPETE
640) 15-KETOEICOSATETRAENOIC ACID
641) 17-Allylamino-geldanamycin
642) 17-OCTADECYNOIC ACID
643) 17-PHENYL-TRINOR-PGE2
644) 1-ACYL-PAF
645) 1-HEXADECYL-2-ARACHIDONOYL-522)
646) GLYCEROL
647) 1-HEXADECYL-2-METHYLGLYCERO-3 PC
648) 1-HEXADECYL-2-O-ACETYL-GLYCEROL
649) 1-HEXADECYL-2-O-METHYL-GLYCEROL
650) 1-OCTADECYL-2-METHYLGLYCERO-3 PC
651) 1-OLEOYL-2-ACETYL-GLYCEROL
652) 1-STEAROYL-2-LINOLEOYL-GLYCEROL
653) 1-STEAROYL-2-ARACHIDONOYL-GLYCEROL
654) 2,5-ditertbutylhydroquinone
655) 24(S)-hydroxycholesterol
656) 24,25-DIHYDROXYVITAMIN D3
657) 25-HYDROXYVITAMIN D3
658) 2-ARACHIDONOYLGLYCEROL
659) 2-FLUOROPALMITIC ACID
660) 2-HYDROXYMYRISTIC ACID
661) 2-methoxyantimycin A3
662) 3,4-dichloroisocoumarin
663) granzyme B inhibitor
664) 4-AMINOPYRIDINE
665) 4-HYDROXYPHENYLRETINAMIDE
666) 4-OXATETRADECANOIC ACID
667) 5(S)-HETE
668) 5(S)-HPETE
669) 5,6-EPOXYEICOSATRIENOIC ACID
670) 5,8,11,14-EICOSATETRAYNOIC ACID
671) 5,8,11-EICOSATRIYNOIC ACID
672) 5-HYDROXYDECANOATE
673) 5-iodotubercidin TABLE 2-continued Culture Variables 674) 5-KETOEICOSATETRAENOIC ACID
675) 5'-N-Ethylcarboxamidoadenosine (NECA)
676) 6,7-ADTN HBr
677) 6-FORMYLINDOLO [3,2-B] CARBAZOLE
678) 7,7-DIMETHYLEICOSADIENOIC ACID
679) 8,9-EPOXYEICOSATRIENOIC ACID
680) 8-methoxymethyl-IBMX
681) 9(S)-HODE
682) 9(S)-HPODE
683) 9,10-OCTADECENOAMIDE
684) A-3
685) AA-861
686) acetyl (N)-s-farnesyl-1-cysteine
687) ACETYL-FARNESYL-CYSTEINE
688) Ac-Leu-Leu-Nle-CHO
689) ACONITINE
690) actinomycin D
691) ADRENIC ACID (22:4, n-6)
692) 1 mM
693) AG-1296
694) AG1478
695) AG213 (Tyrphostin 47)
696) AG-370
697) AG-490
698) AG-879
699) AGC
700) AGGC
701) Ala-Ala-Phe-CMK
702) alamethicin
703) Alrestatin
704) AM 92016
704) AM-251
706) AM-580
707) AMANTIDINE
708) AMILORIDE
709) Amino-1,8-naphthalimide [4-Amino-1,8-522) naphthalimide]
710) Aminobenzamide (3-ABA) [3-522) aminobenzamide (3-ABA)]
711) AMIODARONE
712) ANANDAMIDE (18:2, n-6)
713) ANANDAMIDE (20:3, n-6)
714) ANANDAMIDE (20:4, n-6)
715) ANANDAMIDE (22:4, n-6)
716) anisomycin
717) aphidicolin
718) ARACHIDONAMIDE
719) ARACHIDONIC ACID (20:4, n-6)
720) ARACHIDONOYL-PAF
721) aristolochic acid
722) Arvanil
723) ascomycin (FK-520)
724) B581
725) BADGE
726) bafilomycin A1
727) BAPTA-AM
728) BAY 11-7082
729) BAY K-8644
730) BENZAMIL
731) BEPRIDIL
732) Bestatin
733) beta-lapachone
734) Betulinic acid
735) bezafibrate
736) Blebbistatin
737) BML-190
738) Boc-GVV-CHO
739) bongkrekic acid
740) brefeldin A
741) Bromo-7-nitroindazole [3-Bromo-7-nitroindazole]
742) Bromo-cAMP [8-Bromo-cAMP]
743) Bromo-cGMP [8-Bromo-cGMP]
744) bumetanide
745) BW-B 70C
746) C16 CERAMIDE
747) C2 CERAMIDE
748) C2 DIHYDROCERAMIDE
749) C8 CERAMIDE
750) C8 CERAMINE
750) C8 DIHYDROCERAMIDE
751) CA-074-Me
753) calpeptin
754) calphostin C
755) calyculin A
756) camptothecin
757) cantharidin
758) CAPE
759) capsacin(E)
760) capsazepine
761) CARBACYCLIN
762) castanospermine
763) CDC
764) Cerulenin
765) CGP-37157
766) chelerythrine
767) CIGLITAZONE
768) CIMATEROL
769) CinnGEL 2Me
770) CIRAZOLINE
771) CITCO
772) CLOFIBRATE
773) clonidine
774) CLOPROSTENOL Na
775) clozapine
776) C-PAF
777) Curcumin
778) Cyclo [Arg-Gly-Asp-D-Phe-Val]
779) cycloheximide
780) protein synthesis inhibitor
781) cycloheximide-N-ethylethanoate
782) cyclopamine
783) CYCLOPIAZONIC ACID
784) cyclosporin A
785) cypermethrin
786) cytochalasin B
787) cytochalasin D
788) D12-PROSTAGLANDIN J2
789) D609
790) damnacanthal
791) DANTROLENE
792) decoyinine
793) Decylubiquinone
794) deoxymannojirimycin(1)
795) deoxynorjrimycin(1)
796) Deprenyl
797) DIAZOXIDE
798) dibutyrylcyclic AMP
799) dibutyrylcyclic GMP
800) DICHLOROBENZAMIL
801) DIHOMO-GAMMA-LINOLENIC ACID
802) DIHYDROSPHINGOSINE
803) DIINDOLYLMETHANE
804) DILTIAZEM
805) diphenyleneiodonium Cl
806) dipyridamole
807) DL-DIHYDROSPHINGOSINE
808) DL-PDMP
809) DL-PPMP
810) DOCOSAHEXAENOIC ACID (22:6 n-3)
811) DOCOSAPENTAENOIC ACID
812) DOCOSATRIENOIC ACID (22:3 n-3)
813) doxorubicin TABLE 2-continued Culture Variables 814) DRB
815) E-4031
816) E6 berbamine
817) E-64-d
818) Ebselen
819) EHNA HCl
820) EICOSA-5,8-DIENOIC ACID (20:2 n-12)
821) EICOSADIENOIC ACID (20:2 n-6)
822) EICOSAPENTAENOIC ACID (20:5 n-3)
823) EICOSATRIENOIC ACID (20:3 n-3)
824) ENANTIO-PAF C16
825) epibatidine (+/−)
826) etoposide
827) FARNESYLTHIOACETIC ACID
828) FCCP
829) FIPRONIL
830) FK-506
831) FLECAINIDE
832) FLUFENAMIC ACID
833) FLUNARIZINE
834) FLUPROSTENOL
835) FLUSPIRILINE
836) FPL-64176
837) Fumonisin B1
838) Furoxan
839) GAMMA-LINOLENIC ACID (18:3 n-6)
840) geldanamycin
841) genistein
842) GF-109203X
843) GINGEROL
844) Gliotoxin
845) GLIPIZIDE
846) GLYBURIDE
847) GM6001
848) Go6976
849) GRAYANOTOXIN III
850) GW-5074
851) GW-9662
852) H7]
853) H-89
854) H9
855) HA-1004
856) HA1077
857) HA14-1
858) HBDDE
859) Helenalin
860) Hinokitiol
861) HISTAMINE
862) HNMPA-(AM)3
863) Hoechst 33342 (cell permeable) (BisBenzimide)
864) Huperzine A [(−)-Huperzine A]
865) IAA-94
866) IB-MECA
867) IBMX
868) ICRF-193
869) Ikarugamyin
870) Indirubin
871) Indirubin-3'-monoxime
872) indomethacin
873) juglone
874) K252A
875) Kavain (+/−)
876) KN-62
877) KT-5720
878) L-744,832
879) Latrunculin B
880) Lavendustin A
881) L-cis-DILTIAZEM
882) LEUKOTOXIN A (9,10-EODE)
883) LEUKOTOXIN B (12,13-EODE)

TABLE 2-continued

Culture Variables

884) LEUKOTRIENE B4
885) LEUKOTRIENE C4
886) LEUKOTRIENE D4
887) LEUKOTRIENE E4
888) Leupeptin
889) LFM-A13
890) LIDOCAINE
891) LINOLEAMIDE
892) LINOLEIC ACID
893) LINOLENIC ACID (18:3 n-3)
894) LIPOXIN A4
895) L-NAME
896) L-NASPA
897) LOPERAMIDE
898) LY-171883
899) LY-294002
900) LY-83583
901) Lycorine
902) LYSO-PAF C16
903) Manoalide
904) manumycin A
905) MAPP, D-erythro
906) MAPP, L-erythro
907) mastoparan
908) MBCQ
909) MCI-186
910) MDL-28170
911) MEAD ACID (20:3 n-9)
912) MEAD ETHANOLAMIDE
913) methotrexate
914) METHOXY VERAPAMIL
915) Mevinolin (lovastatin)
916) MG-132
917) Milrinone
918) MINOXIDIL
919) MINOXIDIL SULFATE
920) MISOPROSTOL, FREE ACID
921) mitomycin C
922) ML7
923) ML9
924) MnTBAP
925) Monastrol
926) monensin
927) MY-5445
928) Mycophenolic acid
929) N,N-DIMETHYLSPHINGOSINE
930) N9-Isopropylolomoucine
931) N-ACETYL-LEUKOTRIENE E4
932) NapSul-Ile-Trp-CHO
933) N-ARACHIDONOYLGLYCINE
934) NICARDIPINE
935) NIFEDIPINE
936) NIFLUMIC ACID
937) Nigericin
938) NIGULDIPINE
939) Nimesulide
940) NIMODIPINE
941) NITRENDIPINE
942) N-LINOLEOYLGLYCINE
943) nocodazole
944) N-PHENYLANTHRANILIC (CL)
945) NPPB
946) NS-1619
947) NS-398
948) NSC-95397
949) OBAA
950) okadaic acid
951) oligomycin A
952) olomoucine
953) ouabain
954) PAF C16
955) PAF C18
956) PAF C18:1
957) PALMITYLETHANOLAMIDE
958) Parthenolide
959) PAXILLINE

TABLE 2-continued

Culture Variables

960) PCA 4248
961) PCO-400
962) PD 98059
963) PENITREM A
964) pepstatin
965) PHENAMIL
966) Phenanthridinone [6(5H)-Phenanthridinone]
967) Phenoxybenzamine
968) PHENTOLAMINE
969) PHENYTOIN
970) PHOSPHATIDIC ACID, DIPALMITOYL
971) Piceatannol
972) pifithrin
973) PIMOZIDE
974) PINACIDIL
975) piroxicam
976) PP1
977) PP2
978) prazocin
979) Pregnenolone 16alpha carbonitrile
980) PRIMA-1
981) PROCAINAMIDE
982) PROPAFENONE
983) propidium iodide
984) propranolol (S−)
985) puromycin
986) quercetin
987) QUINIDINE
988) QUININE
989) QX-314
990) rapamycin
991) resveratrol
992) RETINOIC ACID, ALL TRANS
993) REV-5901
994) RG-14620
995) RHC-80267
996) RK-682
997) Ro 20-1724
998) Ro 31-8220
999) Rolipram
1000) roscovitine
1001) Rottlerin
1002) RWJ-60475-(AM)3
1003) RYANODINE
1004) SB 202190
1005) SB 203580
1006) SB-415286
1007) SB-431542
1008) SDZ-201106
1009) S-FARNESYL-L-CYSTEINEME
1010) Shikonin
1011) siguazodan
1012) SKF-96365
1013) SP-600125
1014) SPHINGOSINE
1015) Splitomycin
1016) SQ22536
1017) SQ-29548
1018) staurosporine
1019) SU-4312
1020) Suramin
1021) swainsonine
1022) tamoxifen
1023) Tanshinone IIA
1024) taxol = paclitaxel
1025) TETRAHYDROCANNABINOL-7-OIC ACID
1026) TETRANDRINE
1027) thalidomide
1028) THAPSIGARGIN
1029) Thiocitrulline [L-Thiocitrulline HCl]
1030) Thiorphan
1031) TMB-8
1032) TOLAZAMIDE
1033) TOLBUTAMIDE
1034) Tosyl-Phe-CMK (TPCK)
1035) TPEN
1036) Trequinsin
1037) trichostatin-A
1038) trifluoperazine
1039) TRIM
1040) Triptolide
1041) TTNPB
1042) Tunicamycin
1043) tyrphostin 1
1044) tyrphostin 9
1045) tyrphostin AG-126
1046) tyrphostin AG-370
1047) tyrphostin AG-825
1048) Tyrphostin-8
1049) U-0126
1050) U-37883A
1051) U-46619
1052) U-50488
1053) U73122
1054) U-74389G
1055) U-75302
1056) valinomycin
1057) Valproic acid
1058) VERAPAMIL
1059) VERATRIDINE
1060) vinblastine
1061) vinpocetine
1062) W7
1063) WIN 55,212-2
1064) Wiskostatin
1065) Wortmannin
1066) WY-14643
1067) Xestospongin C
1068) Y-27632
1069) YC-1
1070) Yohimbine
1071) Zaprinast
1072) Zardaverine
1073) ZL3VS
1074) ZM226600
1075) ZM336372
1076) Z-prolyl-prolinal
1077) zVAD-FMK
1078) Ascorbate
1079) 5-azacytidine
1080) 5-azadeoxycytidine
1081) Hexamethylene bisacetamide (HMBA)
1082) Sodium butyrate
1083) Dimethyl sulfoxide.
1084) Goosecoid
1085) Glycogen synthase kinase-3
1086) Galectin-1
1087) Galectin-3

Cell Adhesion Molecules

1086) Cadherin 1 (E-Cadherin)
1087) Cadherin 2 (N-Cadherin)
1088) Cadherin 3 (P-Cadherin)
1089) Cadherin 4 (R-Cadherin)
1090) Cadherin 5 (VE-Cadherin)
1091) Cadherin 6 (K-Cadherin)
1092) Cadherin 7
1093) Cadherin 8
1094) Cadherin 9
1095) Cadherin 10
1096) Cadherin 11 (OB-Cadherin)
1097) Cadherin 12 (BR-Cadherin)
1098) Cadherin 13 (H-Cadherin)
1099) Cadherin 14 (same as Cadherin 18)
1100) Cadherin 15 (M-Cadherin)

TABLE 2-continued

Culture Variables

1101) Cadherin 16 (KSP-Cadherin)
1102) LI Cadherin

The foregoing is exemplary of the factors and conditions that can be used to promote differentiation of ES cells or ED cells along particular developmental lineages. Partially or terminally differentiated endodermal, mesodermal, or ectodermal cell types can be used in screening assays, to study developmental and stem cell biology, or to produce therapeutics. Partially or terminally differentiated cell types can optionally be substantially purified, formulated as pharmaceutical preparations, and/or cryopreserved.

Pluripotency of ES Cells

Pluripotency of the human ES cells or cell lines produced by the methods of this invention can be determined by detecting expression of human ES cell marker proteins. Examples of such proteins include but are not limited to octamer binding protein 4 (Oct-4), stage-specific embryonic antigen (SSEA)-3, SSEA-4, TRA-1-60, TRA-1-81 and alkaline phosphatase. In some embodiments, the putative ES cell lines maintain pluripotency after more than 13, 20, 30, 40, 50, 60, 70, 80, 90 or 100 passages. The ES cells may also be assayed for maintenance of normal karyotype. Pluripotency may also be confirmed by differentiating the ES cell produced by the methods of this invention into cells of ectoderm, endoderm and mesoderm lineage using methods known in the art. Pluripotency may also be tested by transplanting ES cells in vivo, for example into an immunodeficient mouse (such as a SCID mouse), and evaluating teratoma formation.

In certain embodiments, the ES cells or cell lines produced from a blastomere express one or more ES cell marker protein. Additionally or alternatively, in certain embodiments, the cells maintain a normal karyotype. Additionally or alternatively, in certain embodiments, the cells maintain pluripotency after more than 13, 20, 30, 40, 50, 60, 70, 80, 90 or 100 passages.

For any of the foregoing, the ES cell or cell line produced from a blastomere can be generated without destroying the embryo from which the blastomere used to generate the cell or line is obtained. This characteristic of the cells distinguishes these cells from currently available ES cells and lines which were generated using methods that necessarily destroyed the underlying embryo.

Production of TS Cells

This invention also provides methods of directly differentiating cell types from isolated blastomeres before and without generating ES cell lines. In one example, human trophoblast stem ("TS") cells are produced by contacting blastomere outgrowths, which morphologically resemble trophoblast and/or extraembryonic endoderm, but which do not resemble ES cells, with FGF-4. For example, FGF-4 is added to the culture media of the outgrowths. TS cells can be detected by assaying expression of proteins such as cdx-2, fgfr2, PL-1 and human chorionic gonadotropin (hCG) using procedures standard in the art. TS cell identification can also be evidenced by absence of the expression of proteins such as, but not limited to, Oct-4 and α-feto protein.

Production of Purified Preparations and Cell Lines

In certain embodiments, cell lines can be produced. By way of example, once a particular cell type is identified in a culture comprising a cluster of two or more blastomeres (blastomere-derived outgrowths), that cell can be separated from the remainder of the culture for further use. Once separated, the desired cell can be propagated as a purified or substantially purified population, or it can be maintained as a cell line.

In certain embodiments, an ES cell produced from culturing a blastomere obtained from an embryo is separated from the culture of blastomere-derived outgrowths, and an ES cell line is established using standard techniques developed when establishing ES cell lines from blastocyst stage embryos. In other embodiments, a partially differentiated ED cell of interest can be select based on, for example, morphology and that cell can be separated from the culture and purified or otherwise further analyzed.

Exemplary cell lines include stable cell lines. ES cell lines established in this way may have the properties of existing ES cell lines, for example, differentiation potential, protein expression, karyotype, and the like. Alternatively, ES cell lines established in this way may differ from existing ES cell lines in one or more ways.

Therapeutic Uses of ES and ED Cells

The ES or ED cells of this invention are suitable for any use for which ES cells are useful. The present invention provides a method of treating a disorder amenable to cell therapy comprising administering to the affected subject a therapeutically effective amount of the ES cells of the invention.

In one embodiment the methods of the invention are used to remove a blastomere preceding implantation of a human embryo after which the blastomere would be cultured as described above in order to derive and store human ES cells for therapeutic uses using cell therapy should the child resulting from the human embryo require, for example, disease therapy, tissue repair, transplantation, treatment of a cellular debilitation, or treatment of cellular dysfunctions in the future.

In another embodiment of the invention, cells derived from a blastomere, precompaction morula, compacting morula, or sectioned blastocyst are directly differentiated in vitro or in vivo to generate differentiating or differentiated cells without generating an embryonic stem cell line. See U.S. patent publication no. 20050265976, published Dec. 1, 2005, and international patent publication no. WO0129206, published Apr. 26, 2001, the disclosures of which are hereby incorporated by reference herein for methods of direct differentiation. The cells of the invention are useful in medical, veterinary and biological research and in the treatment of disease by providing cells for use in cell therapy, e.g., allogeneic cell therapy.

In another embodiment, an ES cell or cell line is derived from a blastomere and the ES cell or cell line is induced to differentiate to produce one or more mesodermal, endodermal, or ectodermal cell types. Exemplary cell types include, but are not limited to, RPE cells, hematopoietic stem cells, hematopoietic cell types (e.g., RBCs, platelets, etc.), pancreatic beta cells, skin cells, cardiomyocytes, smooth muscle cells, endothelial cells, hepatocytes, neurons, glia, skeletal muscle cells, vascular cells, and the like. Although ES cells may themselves be used in the treatment of diseases or disorders, the invention also contemplates the productions of differentiated cell types that can be used therapeutically.

The methods of the present invention may be used to generate stem cells from blastomeres wherein the stem cells are hemizygous or homozygous for MHC antigens. These cells are useful for reduced immunogenicity during transplantation and cell therapy. The stem cells so produced may be assembled into a bank with reduced complexity in the MHC genes. The blastomeres of this invention could be derived from embryos that are hemizygous or homozygous for MHC antigens. These embryos may be either selected to be hemizygous or homozygous for MHC antigens or made, by any methods known in the art, to be hemizygous or homozygous for MHC antigens. Alternatively stem cells derived from blastomeres may be made hemizygous or homozygous for MHC antigens, e.g., by gene targeting. See, e.g., WO 03/018760 published Mar. 6, 2003 and U.S. provisional patent application No. 60/729, 173 the disclosures of which are incorporated herein in their entirety.

The ES cells and human embryo-derived cells generated by the above-mentioned novel techniques are utilized in research relating to cell biology, drug discovery, and in cell therapy, including but not limited to, production of hematopoietic and hemangioblastic cells for the treatment of blood disorders, vascular disorders, heart disease, cancer, and wound healing, pancreatic beta cells useful in the treatment of diabetes, retinal cells such as neural cells and retinal pigment epithelial cells useful in the treatment of retinal disease such as retinitis pigmentosa and macular degeneration, neurons useful in treating Parkinson's disease, Alzheimer's disease, chronic pain, stroke, psychiatric disorders, and spinal cord injury, heart muscle cells useful in treating heart disease such as heart failure, skin cells useful in treating wounds for scarless wound repair, burns, promoting wound repair, and in treating skin aging, liver cells for the treatment of liver disease such as cirrhotic liver disease, kidney cells for the treatment of kidney disease such as renal failure, cartilage for the treatment of arthritis, lung cells for the treatment of lung disease and bone cells useful in the treatment of bone disorders such as osteoporosis.

Such cell therapy methods may involve use of the ES cells of this invention in combination with proliferation factors, lineage-commitment factors, or gene or proteins of interest. Treatment methods may include providing stem or appropriate precursor cells directly for transplantation where the tissue is regenerated in vivo or recreating the desired tissue in vitro and then providing the tissue to the affected subject.

Pharmaceutical Preparations

The invention provides methods of generating ES cells, ES cell lines, TS cells, and various partially and terminally differentiated cells and cell lines. Cells and cell lines so produced can be studied in vitro and in vivo. In certain embodiments, the study of these cells provides information about basic developmental biology and stem cell biology. In certain other embodiments, the study of these cells and/or the factors that can be used to manipulate the proliferation, differentiation, and survival of these cells can be used to develop stem-cell based therapies to treat or ameliorate any of a variety of diseases or conditions. In other embodiments, cells and cell lines produced by these methods can be used in screening assays to identify agents and conditions that can be used therapeutically. Identified therapeutics may be used to develop cellular therapies or may themselves be useful when delivered to patients.

In certain embodiments, ES cells, ES cell lines, TS cells, TS cell lines, or partially or terminally differentiated cells may be formulated as pharmaceutical preparations by combining the cells with a pharmaceutically acceptable carrier or excipient. In certain embodiments, the pharmaceutical preparation contains a certain number of cells per unit volume of carrier so that cellular therapies can be administered to deliver a particular dosage of cells. For example, pharmaceutical preparations can be formulated to permit delivery of, for example, $1 \times 10^5$, $1 \times 10^6$, $2 \times 10^6$, $3 \times 10^6$, $4 \times 10^6$, $5 \times 10^6$, $1 \times 10^7$, or greater than $1 \times 10^7$ cells in a volume of carrier appropriate for the condition being treated and the route of administration.

Methods of Conducting Research

As detailed above, embryonic stem cell research has been partially hindered by political and ethical opposition to the destruction of embryos. The present invention not only provides an alternative method for efficiently generating cells and cell lines, including ES cells and cell lines, the present invention also provides a method that does not require that new embryos be destroyed as part of the process of ES cell derivation. Remaining embryos can be cryopreserved and perpetually preserved or reserved for additional, future research use.

For some, the ability to derive ES cells and cell lines (or partially or terminally differentiated cell types differentiated from ES cells or directly differentiated from embryos) without necessarily destroying new embryos will provide substantial benefits beyond the significant technical advanced reflected in these methods. As such, the invention provides novel methods of conducting embryonic stem cell research without destroying a human embryo. The method entails obtaining a human ES cell or ES cell line derived from a human embryo but without destroying that human embryo. The ES cell or cell line can be generated from a blastomere obtained from a human embryo using any of the methodologies disclosed herein. Once an ES cell or cell line is derived, the method further entails conducting embryonic stem cell research using the human ES cell or ES cell line. The method provides an avenue for conducting ES cell research without the need to destroy new embryos.

In certain embodiments, the embryonic stem cell research involves research examining the differentiation potential of ES cells or cell lines. For example, the research may involve contacting the human ES cell or ES cell line with one or more factors, and identifying factors that promote differentiation of the ES cell or ES cell line to one or more mesodermal, endodermal, or ectodermal cell types. In other embodiments, the embryonic stem cell research involves the study of possible therapeutic uses of ES cells or cell differentiated there from.

Regardless of the particular research use, this method may expand the opportunities for collaboration with researchers around the world, particularly researchers working in countries with laws regulating embryo destruction.

Unless otherwise defined, all technical and scientific terms used herein have the same meaning as commonly understood by one of ordinary skill in the art. In case of conflict, the present specification, including definitions, will control. Further, unless otherwise required by context, singular terms shall include pluralities and plural terms shall include the singular. Generally, nomenclatures used in connection with, and techniques of, cell and tissue culture, molecular biology, immunology, microbiology, genetics, developmental biology, cell biology described herein are those well-known and commonly used in the art. Exemplary methods and materials are described below, although methods and materials similar or equivalent to those described herein can also be used in the practice or testing of the present invention.

All publications and other references mentioned herein are incorporated by reference in their entirety. Although a number of documents are cited herein, this citation does not constitute an admission that any of these documents forms part of the common general knowledge in the art.

Throughout this specification and claims, the word "comprise," or variations such as "comprises" or "comprising" will be understood to imply the inclusion of a stated integer or group of integers but not the exclusion of any other integer or group of integers.

In order for that this invention may be better understood, the following examples are set forth. These examples are for purposes of illustration only and are not be construed as limiting the scope of the invention in any matter.

Example 1

Generation of Human ES Cell Lines

Unused embryos produced by in-vitro fertilization for clinical purposes were obtained. Six of these embryos were Grade I or II (symmetrical and even cell division with little or no cytoplasmic fragmentation), whereas the remaining ten embryos were Grade III (variable fragmentation) using standard scoring system (Veeck, L. L. et al., *An Atlas of Human Gametes and Conceptuses*, Parthenon, New York, N.Y., 1999). Embryos with blastomeres of unequal size and moderate-to-severe fragmentation (Grades IV and V) were excluded from this study. Pronuclear and multi-cell stage human embryos were thawed and cultured until the 8-10 cell stage at 37 C in 20 µl drops of Quinn's cleavage medium (Cooper Surgical Inc., Cat # ART1526) under paraffin oil (Cooper Surgical Inc. Cat # 4008) in a high humidified incubator with 5.5% $CO_2$/5% $O_2$/89.5% $N_2$.

The zona pellucida was disrupted using either Acidic Tyroides solution or multiple Piezo-pulses and individual blastomeres were mechanically separated from the denuded embryos by holding the embryo with a micropipette and gently tapping the pipette holder. The separated blastomeres were cultured together in the same media (Quinn's cleavage medium (Cooper Surgical Inc., Cat # ART1526)) and arranged so as to avoid contact with each other by using depressions created in the bottom of the plastic tissue culture plate as previously described (Nagy, A. et al., *Manipulating the Mouse Embryos: A Laboratory Manual*, Cold Spring Harbor Laboratory Press, Cold Spring Harbor, N.Y. 2002).

The majority (58%) of the isolated blastomeres divided at least once and approximately half of these (28 out of 53) formed vesicles or clumps which produced cellular outgrowths within 2-3 days (FIG. 1B,C). During this process, sets of microdrops were prepared consisting of a 50 µl drop of blastomere medium (Quinn's blastocyst medium, Coopers Surgical Inc. Cat # ART1529) containing a blastomere-derived aggregate surrounded by several microdrops of hES culture medium (Knockout-DMEM (Invitrogen Cat # 10829-018 supplemented with 5% plasmanate, 5% serum replacement, 10% fetal bovine serum, 20 ng/ml leukemia inhibiting factor (LIF) and 8-16 ng/ml basic fibroblast growth factor (bFGF)) containing green fluorescent protein (GFP)-labeled hES cells growing on a mitomycin C-treated mouse embryonic fibroblasts (MEF) feeder layer. Previous experiments in mice (Chung et al., *Nature* (2006) 439:216-219) indicated that cell co-culture is important for ES cell derivation from single blastomeres. However, the aggregation system used in these previous studies could not be employed because, unlike in the mouse, human blastomeres do not form tight aggregates with ES cells. Thus, the microdrops containing the blastomere-derived vesicles/clumps were merged with one or two surrounding microdrops seeded with mitomycin-C treated mouse embryonic fibroblasts (MEFs) and GFP-positive human embryonic stem (hES) cells by scraping the bottom of the plate between the drops with a glass capillary.

After formation of initial outgrowths approximately half of the medium was changed every other day until the outgrowths reached approximately 50-100 cells. Although the initial outgrowths generally contained cells of different morphologies over a period of several days we observed several fates: (1) cells resembling trophectoderm took over, (2) cells that initially resembled ES-cells differentiated, or (3) ES-like cells continued undifferentiated proliferation. All of these outcomes are typical of derivation of ES cells from human embryos, especially when intact blastocysts are plated without removal of the trophectoderm using immunosurgery. The putative human ES cells were mechanically passaged onto fresh MEF feeder layers in hES culture medium which was changed every 1-2 days. The colonies were passaged by mechanical dispersion and transferred to fresh feeders every 2-3 days until enough cells were produced to initiate adaption to trypsin. The colony morphology, growth rate, procedures and culture media used were very similar to those of blastocyst-derived ES cells.

Karyotyping of the cells derived from the human blastomere were determined using the following procedure: Cells were passaged onto gelatin in ES culture medium which was replaced the day before harvest until the cells were approximately 50% confluent. Colcemid (Invitrogen) was added to the culture at a concentration of 0.12 µg/ml for 40 minutes. The cells were then rinsed twice with PBS and then trypsinized and centrifuged in DMEM (Invitrogen) with 10% FBS (Hyclone). 0.075 M KCl was added to the pellet and the cells were incubated for 10 minutes at 37° C. The cells were then centrifuged and fixed with 3:1 methanol/acetic acid (Baker) for 10 minutes, centrifuged again and suspended in this fixative. Cytogenetic analysis was performed on metaphase cells using G-banding on 10 cells.

Figure 3:
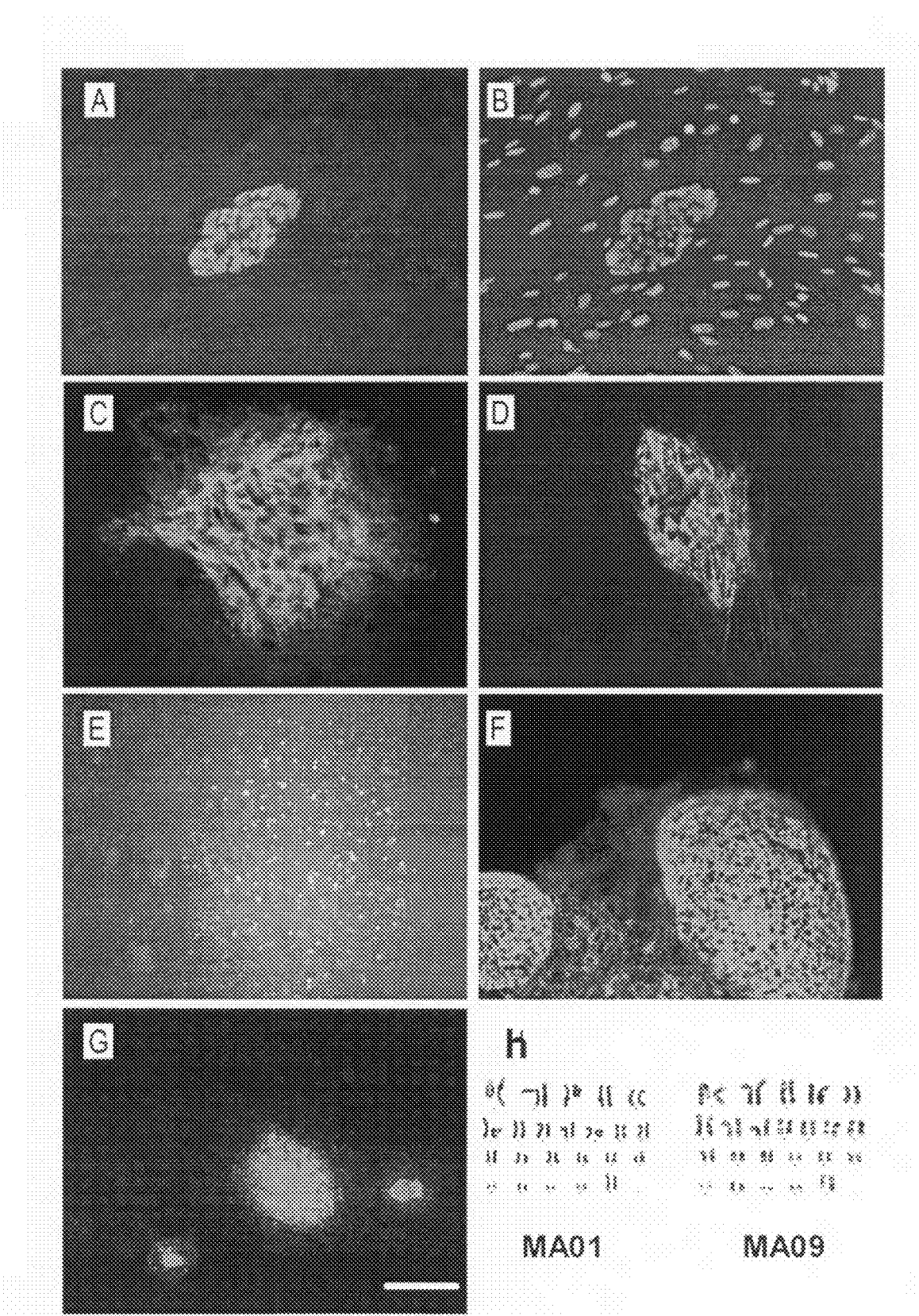
FIG. 3 shows the results of characterizing human ES cells derived from single blastomeres.
Figure 7:
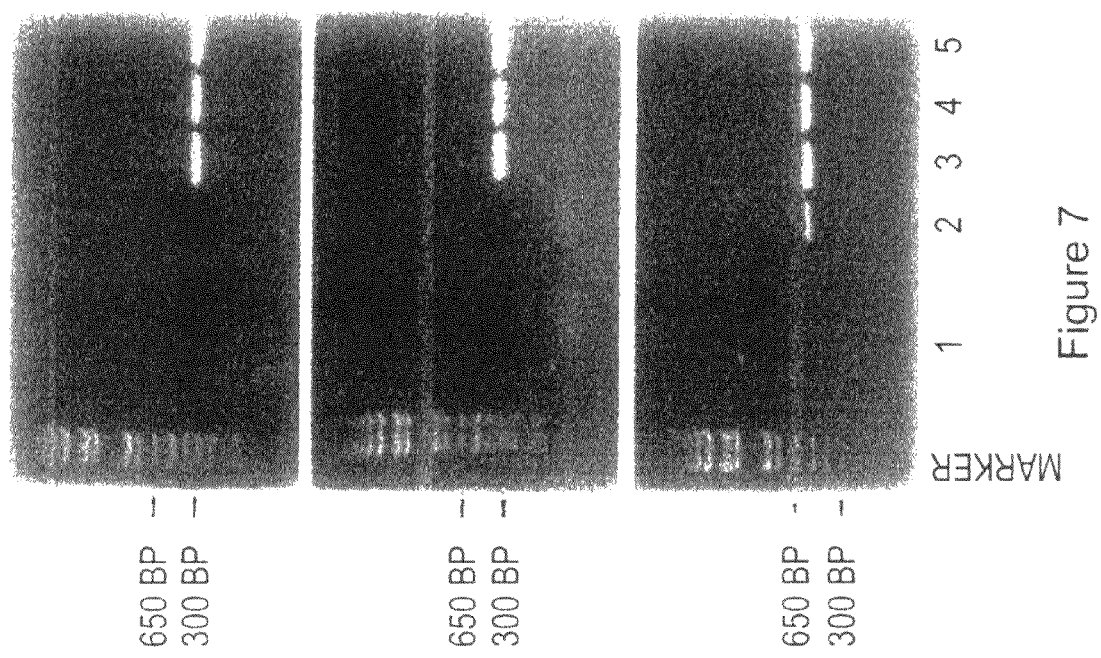
FIG. 7 shows the results of RT-PCR analysis of the expression of markers of pluripotency in single blastomere-derived hES cells lines. Top panel, Oct-4; center panel, nanog; bottom panel, GAPDH. Lane 1, no template; lane 2, negative control (MEFs); lane 3, MA01; lane 4, MA09; lane 5, WA01.

Results of these experiments are shown in Table 1. The results in row 10 of Table 1 were obtained using the method of isolating ES cells as described in Chung et al., *Nature* (2006) 439:216-219. Nineteen ES cell like outgrowths and two stable human ES cell lines (MA01 and MA09) were obtained. The MA01 and MA09 cell lines maintained undifferentiated proliferation for more than seven months. Although the initial outgrowths generally contained cells of different morphologies, over a period of several days, fates typical of derivation of ES cells from human blastocysts were observed. For example, two of the six grade I/II embryos used generated stable hES cell lines that exhibited normal karyotype (line MA01 46, XX; line MA09 46, XX; FIG. 3(*h*)) and maintained molecular markers of pluripotency up to more than 25 passages (FIG. 3(*a*) to (*g*)). Both lines are also positive for alkaline phosphatase and express Oct-4, SSEA-3, SSEA-4, TRA-1-60 and TRA-1-81 (FIG. 7). Microsatellite analysis ruled out contamination of the lines with the ES cells used for co-culture with other hES cell lines in the laboratory. Karyotype and microsatellite analysis ruled out fusion (both new lines were female and the WA01 human ES cells used for co-culture were male) (FIG. 5(*d*)).

Figure 5:
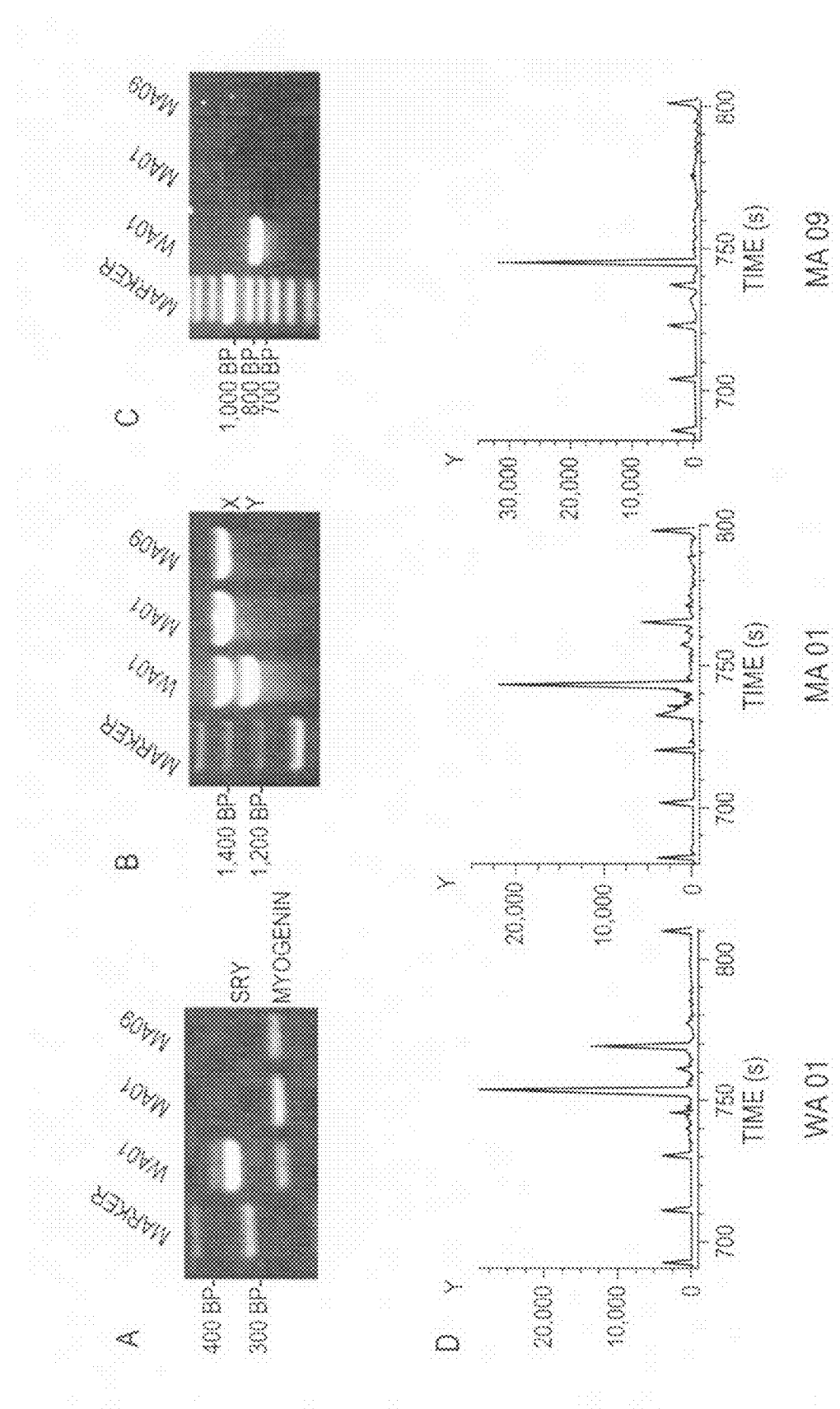
FIG. 5 shows microsatellite and PCR analysis of single blastomere-derived human ES cell lines (MA01 and MA09) and the cell line (WA01) used for co-culture.

Polymerase chain reaction (PCR) analysis further confirmed the absence of GFP and Y-chromosome gene sequences in both blastomere-derived human ES cell lines (FIG. 5(*a*) to (*c*)). Conventional PCR reactions were performed with 100 ng genomic DNA, Amplitaq Gold polymerase (ABI, Foster City, Calif.), and primer pairs specific for FES/FPS, vWA31, D22S417, D10S526 and D5S592 genomic microsatellite sequences (Coriell, Camden, N.J.). Single primers in each pair were end-labeled with a 6-Fam fluorescent label. After incubation for 10 min at 94° C. to activate the polymerase, amplification was performed with 30 cycles of 94° C. for 45 sec, 56° C. for 60 sec, and 72° C. for 60 sec. Labeled amplicons were separated and sized using an ABI 3730 sequencer. For amplification of eGFP, amelogenin and SRY genes, genomic DNA was isolated using a QIAamp DNA Mini Kit (Qiagen), and 200 ng DNA per reaction in 50 μl was used for eGFP, amelogenin and SRY amplification. Primers used for eGFP were forward 5'-TTGAATTCGC-CACCATGGTGAGC-3' (SEQ ID NO: 1) and reverse 5'-TTGAATTCTTACTTGTACAGCTCGTCC-3' (SEQ ID NO: 2) and PCR reactions were performed as described previously. For sex determination, both amelogenin and SRY genes were amplified by PCR. Primers used for amelogenin gene were forward 5'-CTCATCCTGGGCACCCTGGT-TATATC-3' (SEQ ID NO: 3), reverse, 5'-GGTACCACT-TCAAAGGGGTAAGCAC-3' (SEQ ID NO: 4), which generated a fragment of 1310 bp for Y-chromosome and a fragment of 1490 bp for X-chromosome. For Y-chromosome specific SRY gene, primers used were forward 5'-GATCAG-CAAGCAGCTGGGATACCAGTG-3' (SEQ ID NO: 5), and reverse 5'-CTGTAGCGGTCCCGTTGCTGCGGTG-3' (SEQ ID NO: 6), which amplified a DNA fragment of 330 bp. As a control for PCR reactions, myogenin primers, forward 5'-TCACGGTGGAGGATATGTCT-3' (SEQ ID NO: 7) and reverse 5'-GAGTCAGCTAAATTCCCTCG-3' (SEQ ID NO: 8) were included in SRY PCR reactions, which generated a fragment of 245 bp. PCR products were separated on an agarose gel and visualized by ethidium bromide staining.

Figure 4:
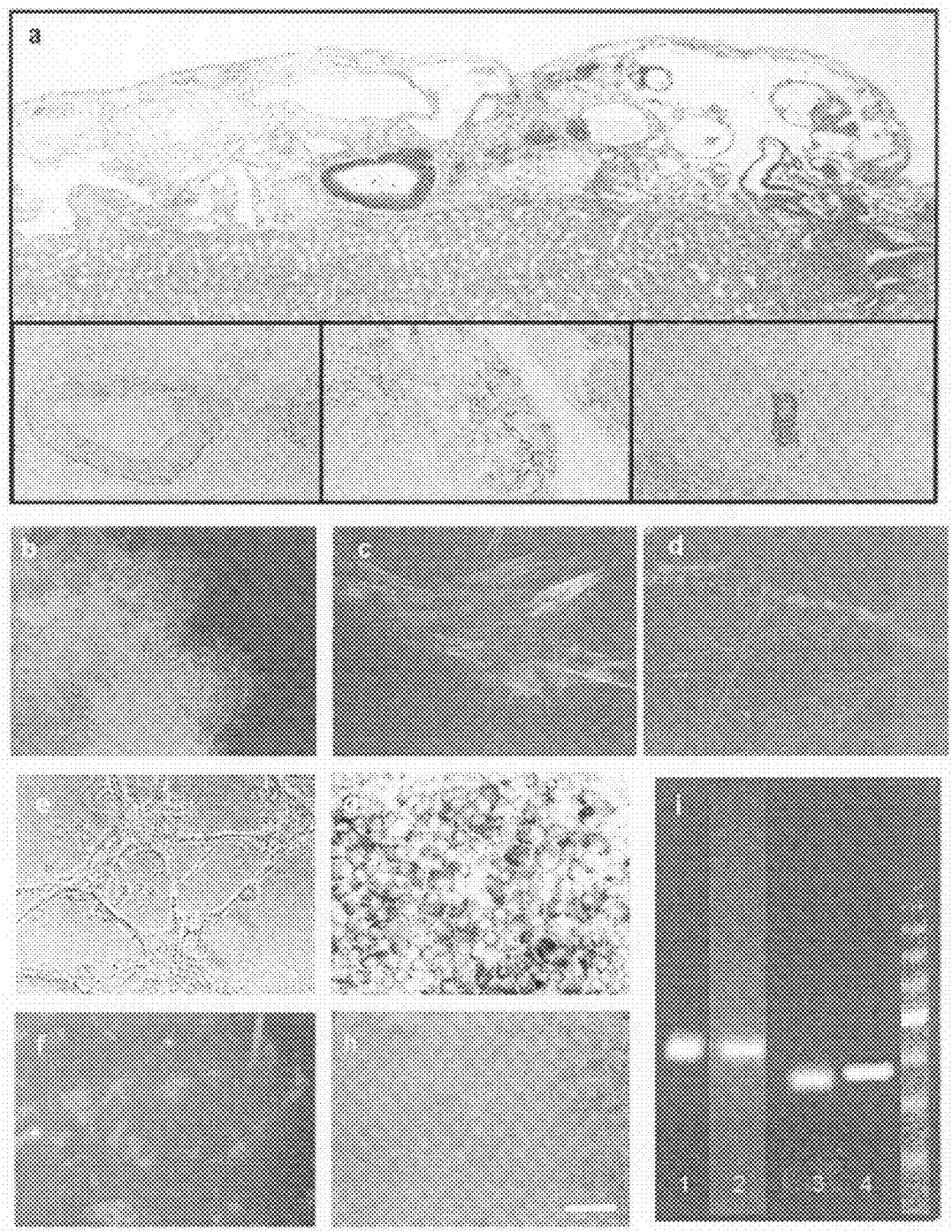
FIG. 4 shows the in vitro differentiation of single blastomere-derived human ES cells into all three germ layers.

Although only two of the six (33%) grade I/II embryos (or 2 out of the 35 blastomeres; 2 out of 91 blastomeres including grade III-V embryos) generated hES cell lines, this success rate is similar to that produced using conventional methods. We believe the success rate can be further increased by optimizing conditions at the earliest stages of blastomere outgrowth.

tives from endoderm, mesoderm and ectoderm using tissue specific antibodies (α-feto protein for primitive endoderm, muscle actin for mesoderm, and β III tubulin for ectoderm) (FIG. 4).

Figure 8:
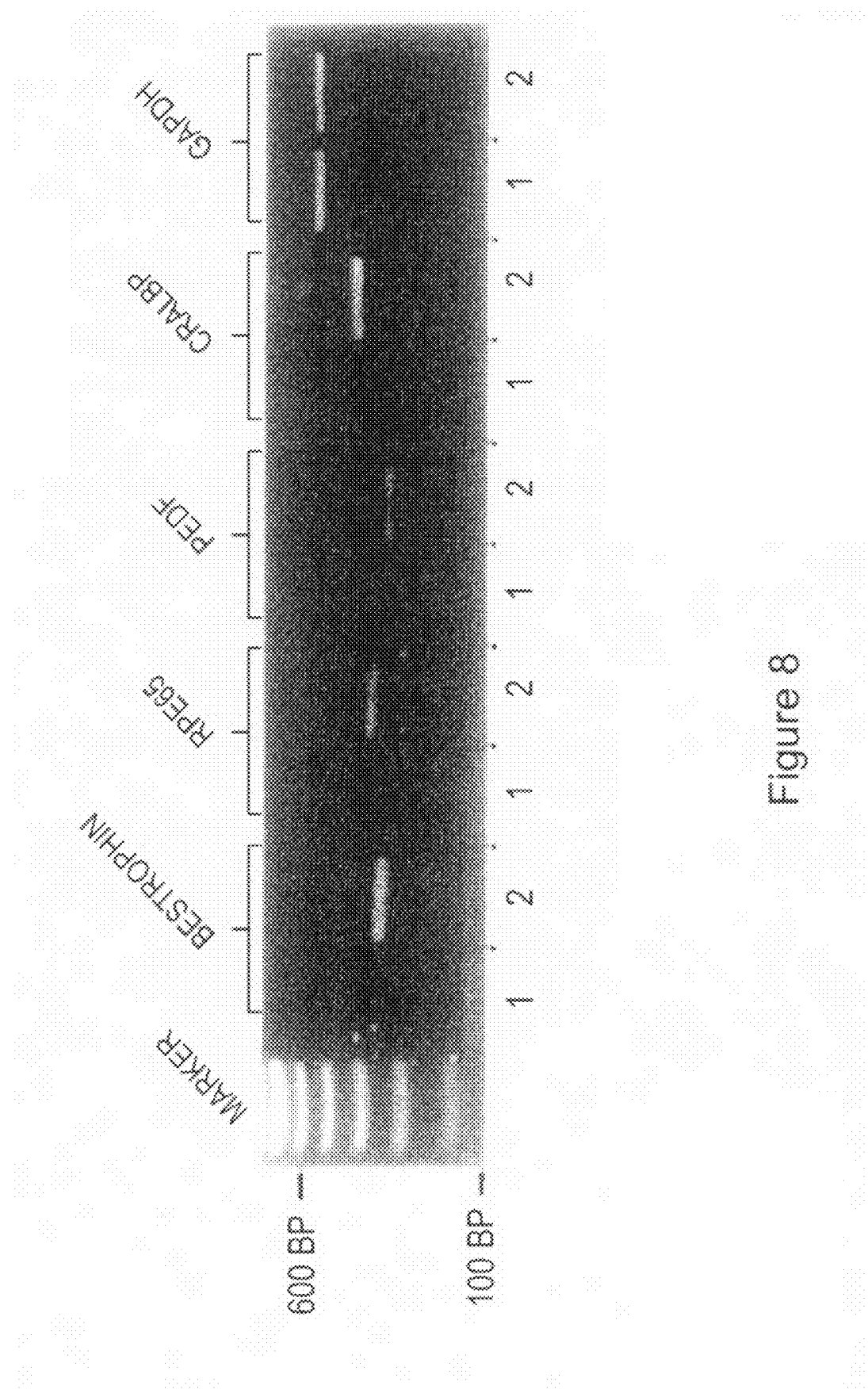
FIG. 8 shows the results of RT-PCR analysis for markers of RPE in single-blastomere-derived RPE. For each gel: lane 1, negative control (undifferentiated hES cells, line WA09); lane 2, RPE from hES cells.

The single blastomere-derived human ES cell could also be differentiated in vitro into cells of specific therapeutic interest, including endothelial cells which after replating on Matrigel, formed typical capillary-vascular like structures (FIG. 4(e)) that expressed high levels of von Willebrand Factor (vWF) and took up acetylated low-density-lipoprotein (Ac-LDL) (FIG. 4(f)). Retinal pigment epithelium (RPE) clusters also appeared in adherent human ES cell cultures and in embryoid bodies and were used to establish passageable RPE lines using methods known in the art. These RPE lines displayed pigmented phenotype and typical "cobblestone" morphology (FIG. 4(g)), bestrophin immunostaining (FIG. 4(h)) and expressed bestrophin, RPE65, CRALBP and PEDF as shown by RT-PCR (FIG. 4(i) and FIG. 8).

To induce teratomas, small clumps of 50-100 hES cells were mechanically removed from the culture and transplanted under the kidney capsules of 6-8 week old NOD-SCID mice under anesthesia. After 2-3 weeks, the kidneys were removed, fixed with 4% paraformaldehyde overnight, washed for 24 hours in PBS, embedded in paraffin, sectioned and analyzed for the presence of the derivatives of three germ layers: endoderm, mesoderm and ectoderm. Alternatively, approximately 1 million hES cells were injected into the rear thigh of NOD-SCID mice. After approximately two months the mice were sacrificed and the teratomas excised, fixed in 4% paraformaldehyde, embedded in paraffin and sectioned.

TABLE 1

Embryonic stem-cells derived from single human blastomeres

| Exp. No. | No. embryos used | No. blastomeres retrieved | No. blastomeres that divided | No. outgrowths | No. ES cell-like outgrowths | No. ES cell lines established | Comments |
|---|---|---|---|---|---|---|---|
| 1 | 2 | 10 | 4 | 1 | 0 | 0 | w/o ES co-culture |
| 2 | 1 | 6 | 3 | 0 | 0 | 0 | w/o ES co-culture |
| 3 | 2 | 11 | 6 | 5 | 4 | 1 | ES co-culture |
| 4 | 1 | 7 | 6 | 1 | 1 | 0 | ES co-culture |
| 5 | 2 | 12 | 7 | 3 | 3 | 0 | ES co-culture |
| 6 | 2 | 12 | 7 | 5 | 4 | 1 | ES co-culture |
| 7 | 2 | 11 | 7 | 4 | 3 | 0 | ES co-culture |
| 8 | 1 | 6 | 3 | 0 | 0 | 0 | ES co-culture |
| 9 | 1 | 4 | 3 | 3 | 2 | 0 | ES co-culture |
| 10 | 2 | 12 | 7 | 6 | 2 | 0 | ES aggregation (different technique) |
| Total | 16 | 91 | 53 | 28 | 19 | 2 | |
| 1 | ADD | ADD | ADD | DSGRFHSDGHFGHFGH | | | |
| 2 | ADD | ADD | ADD | DSGRFHSDGHFGHFGH | | | |

Example 2

Differentiation of Human ES Cells

The ability of the human ES cells to differentiate into different germ layers was analyzed both in vitro and in teratomas using techniques known in the art.

Briefly, for the in vitro experiments, the human ES cells were separated by treating with either collagenase or trypsin and then cultured in cell culture dishes without feeder cells in embryoid body (EB) medium. Approximately one week later, the ES cells formed embryoid bodies (EB). The EBs were then fixed in 4% formaldehyde, washed in PBS, embedded in paraffin, sectioned and analyzed for the presence of deriva- The presence of different germ layers was assayed by determining the presence of molecular markers: β III tubulin for ectoderm, smooth muscle actin for mesoderm, and α-feto protein for endoderm (FIGS. 1F-H). The teratomas contained tissues from all three germ layers including neural rosettes (ectoderm), liver and hematopoietic cells (mesoderm) and liver, respiratory and intestinal epithelia (endoderm) among others (FIG. 4(a)). For immunohistochemical analysis, cells were fixed with 2% paraformaldehyde, permeabilized with 0.1% NP-40 and blocked with 10% goat serum, 10% donkey serum (Jackson Immunoresearch Laboratories, West Grove, Pa.) in PBS (Invitrogen) for one hour. Incubation with primary antibodies was carried out overnight at 4 C. After washing in PBS containing 0.1% Tween-20, fluorescently labeled or biotinylated secondary antibodies (Jackson Immunoresearch Laboratories, West Grove, Pa.) were added for one hour; some samples were subsequently incubated for 15 minutes with fluorescently labeled Steptavidin (Amersham, Piscataway, N.J.). After additional washing in PBS/Tween, specimens were mounted using Vectashield with DAPI (Vector Laboratories, Burlingame, Calif.) and observed using a fluorescent microscope (Nikon). Alkaline phosphatase was detected using the Vector Red kit (vector Laboratories, Burlingame, Calif.) according to the manufacturer's instructions. Antibodies used were anti-Oct-4 (Santa Cruz Biotechnology, Santa Cruz, Calif.), anti-SSEA-3, anti-SSEA-4 (Developmental Studies Hybridoma Bank, University of Iowa), anti-TRA-1-60, anti-TRA-1-81 (Chemicon), tubulin β III (BABCO, Berkeley, Calif.), anti-α-feto protein (DACO), and anti-smooth muscle actin (Sigma-Aldrich).

The blastomere-derived cell lines MA01 and MA09 appear to differentiate more readily into certain cell types, For example, neural progenitors were generated without the need for embryoid intermediates, stromal feeder layers or low-density passaging. When transferred to laminin-coated substrate and maintained in defined medium containing laminin and basic fibroblast growth factor, they began to express neuronal and neuronal progenitor markers such as Nestin, β III tubulin and Pax6. MA01 human ES cells also formed hematopoietic colony forming units (CFU) 3-5 times more efficiently than WA01 (H1)-GFP cells and 5-10 times more efficiently than WA09 (H9) cells. MA09 human ES cells showed similar potential as WA 09 cells for hemaopoietic differentiation but demonstrated higher capability to differentiate toward endothelial lineage as compared to both WA01-GFP and WA09 cells.

Example 3

Production of ED Cells

Figure 6:
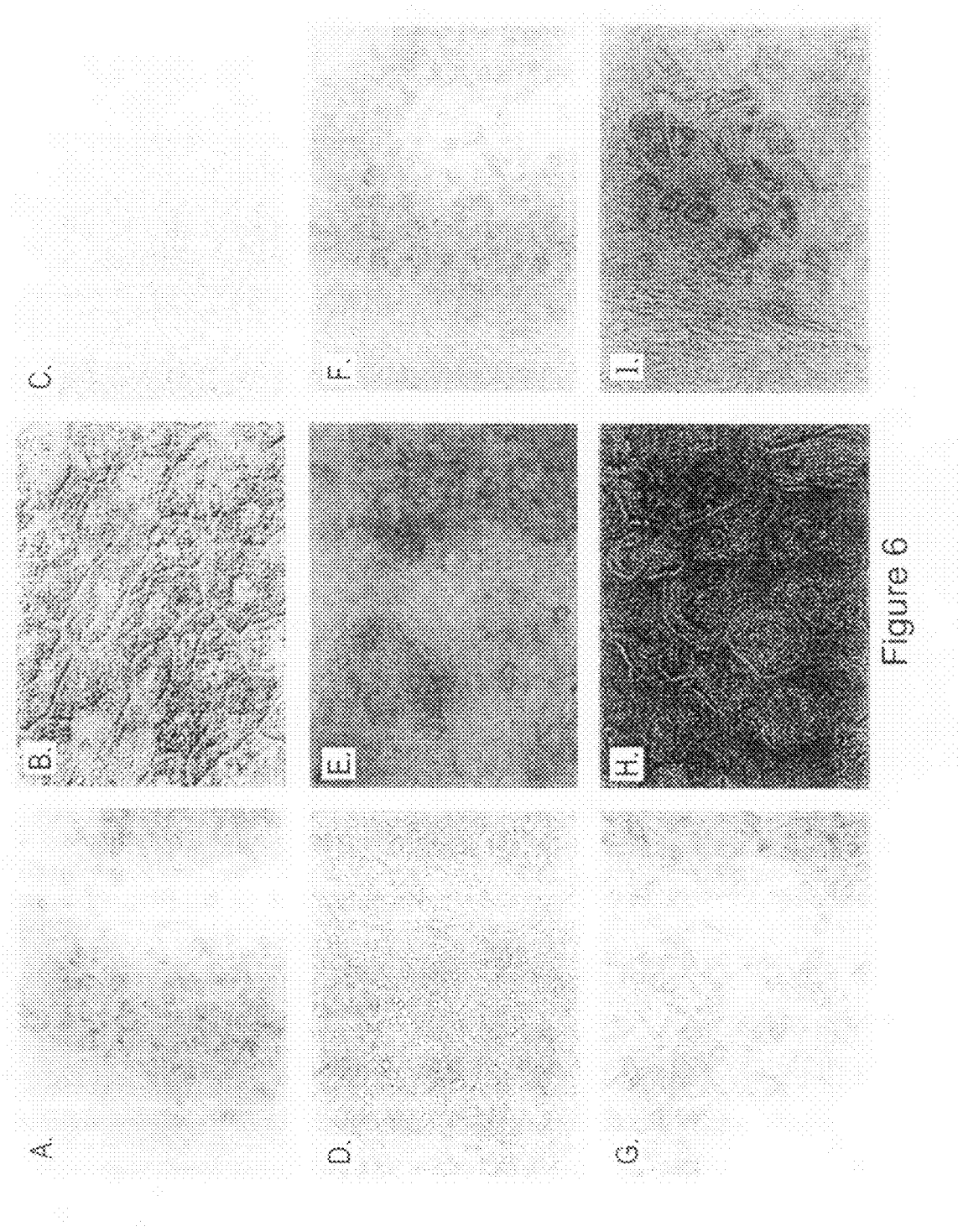
FIG. 6 (a-i) shows photographs of different morphologies of embryo-derived directly-differentiated cells originating from isolated blastomeres in the absence of such blastomeres leading to hES cell lines.

As can be seen in Table 1 above, the production of embryo-derived cells from isolated blastomeres occurs more often than the production of ES cell lines. Of 53 isolated blastomeres that divided, 19 cultures yielded directly-differentiated cell types and only 2 yielded ES cell lines. FIG. 6 shows the variety of differentiated cell morphologies observed by direct differentiation.

Example 4

Production of ED-Derived Endoderm and Pancreatic Beta Cells

Isolated blastomeres as described herein or similar ED cells are added onto mitotically-inactivated feeder cells that express high levels of NODAL or cell lines that express members of the TGF beta family that activate the same receptor as NODAL such as CM02 cells that express relatively high levels of Activin-A, but low levels of Inhibins or follistatin. The cells are then incubated for a period of five days in DMEM medium with 0.5% human serum. After five days, the resulting cells which include definitive endodermal cells are purified by flow cytometry or other affinity-based cell separation techniques such as magnetic bead sorting using an antibody specific to the CXCR4 receptor and then permeabilized and exposed to cellular extracts from isolated bovine pancreatic beta cells as described in U.S. application Ser. No. 11/025,893 (published as US 20050265976), which is incorporated by reference. The resulting cells that have been induced toward beta cell differentiation are then cloned using techniques described in international patent application no. PCT/US2006/013573 filed Apr. 11, 2006 and U.S. Application No. 60/835,779, filed Aug. 3, 2006, the disclosure of which are incorporated by reference. These cells are then directly differentiated into pancreatic beta cells or beta cell precursors using techniques known in the art for differentiating said cells from human embryonic stem cell lines or by culturing the cells on inducer cell mesodermal cell lines (see international patent application no. PCT/US2006/013573 filed Apr. 11, 2006 and U.S. Application No. 60/835,779, filed Aug. 3, 2006, the disclosure of which are incorporated by reference).

Example 5

Derivation of Embryonic Stem Cells without Destruction of the Embryo

Embryos produced by in-vitro fertilization for clinical purposes are obtained. Pronuclear and multi-cell stage human embryos are thawed and cultured until the 8-10 cell stage at 37° C. in 20 μl drops of Quinn's cleavage medium (Cooper Surgical Inc., Cat # ART1526) under paraffin oil (Cooper Surgical Inc. Cat # 4008) in a high humidified incubator with 5.5% $CO_2$/5% $O_2$/89.5% $N_2$.

The zona pellucida is disrupted using either Acidic Tyroides solution or multiple Piezo-pulses and an individual blastomere is mechanically separated from each denuded embryo by holding the embryo with a micropipette and gently tapping the pipette holder. The embryos are subsequently cryopreserved.

The separated blastomeres are cultured as in Example 1.

Example 6

Isolation of a Single Blastomere for Derivation of Embryonic Stem Cells and Pre-Implantation Genetic Diagnosis Embryos produced by in-vitro fertilization for clinical purposes are obtained. Pronuclear and multi-cell stage human embryos are thawed and cultured until the 8-10 cell stage at 37° C. in 20 μl drops of Quinn's cleavage medium (Cooper Surgical Inc., Cat # ART1526) under paraffin oil (Cooper Surgical Inc. Cat # 4008) in a high humidified incubator with 5.5% $CO_2$/5% $O_2$/89.5% $N_2$.

The zona pellucida is disrupted using either Acidic Tyroides solution or multiple Piezo-pulses and an individual blastomere is mechanically separated from the denuded embryo by holding the embryo with a micropipette and gently tapping the pipette holder. The embryo is subsequently cryopreserved.

The separated blastomere undergoes cell division. One progeny cell is used for genetic testing and a different progeny cell is cultured as in Example 1 to produce a human ES cell.

We claim:

1. An in vitro method of producing human embryonic stem (ES) cells from a blastomere, comprising:
    (a) providing a blastomere isolated from a human embryo;
    (b) culturing the blastomere until said blastomere gives rise to a cluster of two or more progeny blastomeres;
    (c) culturing the cluster of two or more progeny blastomeres with human pluripotent cells to obtain a culture of human ES cells that originate from the cluster of progeny blastomeres;
    (d) isolating the human ES cells that originate from the cluster of progeny blastomeres of step (c).

2. The method of claim 1, wherein the culture of step (b) comprises culturing said blastomere isolated from the human embryo of step (a) with the remaining human embryo from which said blastocyst was isolated.

3. The method of claim 1, wherein step (b) comprises culturing in a medium containing less than 5 mM glucose.

4. The method of claim 1, wherein step (b) comprises culturing in a medium containing less than 5 mM glucose and having an osmolarity less than 310 mOsm/kg.

5. The method of claim 1, wherein step (b) comprises culturing in a medium having an osmolarity between about 260 and about 280 mOsm/kg.

6. The method of claim 1, wherein step (b) comprises culturing in a medium containing less than 5 mM glucose and having an osmolarity between about 260 and about 280 mOsm/kg.

7. The method of claim 1, wherein the cluster of two or more progeny blastomeres obtained in step (b) contains 16 or fewer blastomeres.

8. The method of claim 1, wherein the human embryo of step (a) is between the two cell stage and the stage prior to compaction of the morula.

9. The method of claim 1, wherein the human embryo of step (a) is between the four-cell stage and the sixteen-cell stage.

10. The method of claim 1, wherein the human embryo of step (a) is undergoing compaction of the morula.

11. The method of claim 1, wherein the pluripotent cells of step (c) are selected from the group consisting of ES cells, embryonic germ cells, and embryonic carcinoma cells.

12. The method of claim 1, wherein step (c) comprises culturing in a medium selected from the group consisting of: media containing at least 5 mM glucose, media having an osmolarity of at least 310 mOsm/kg, and a medium containing at least 5 mM glucose and having an osmolarity of at least 310 mOsm/kg.

13. The method of claim 1, wherein said providing step of (a) yields said blastomere and a viable human embryo from which the blastomere was obtained.

14. The method of claim 13, wherein the remaining human embryo is cryopreserved following obtaining the blastomere.

15. The method of claim 1, wherein the blastomere is obtained by immobilizing the embryo and tapping the immobilized embryo until the blastomere is isolated.

16. The method of claim 1, further comprising performing genetic testing on at least one progeny cell of said blastomere.

17. An in vitro method of producing human embryonic stem (ES) cells from a blastomere, comprising:
   (a) providing a blastomere isolated from a human embryo;
   (b) culturing the blastomere in a culture comprising two or more human blastomeres until said blastomere isolated from the human embryo gives rise to a cluster of two or more progeny blastomeres; and
   (c) culturing the cluster of two or more progeny blastomeres with human ES cells, thereby producing a culture containing of human ES cells that originate from the cluster of two or more progeny blastomeres;
   (d) isolating the human ES cells that originate from the cluster of two or more progeny blastomeres.

18. The method of claim 17, wherein step (b) comprises culturing in a medium having an osmolarity between about 260 and about 280 mOsm/kg.

19. The method of claim 17, wherein the cluster of two or more progeny blastomeres obtained in step (b) contain 16 or fewer blastomeres.

20. The method of claim 17, wherein the human embryo of step (a) is between the two-cell stage and the stage where the embryo is undergoing compaction of the morula.

21. The method of claim 17, wherein step (c) comprises culturing in a medium selected from the group consisting of: media containing at least 5 mM glucose, media having an osmolarity of at least 310 mOsm/kg, and a medium containing at least 5 mM glucose and having an osmolarity of at least 310 mOsm/kg.

22. The method of claim 17, wherein said providing step of (a) yields said blastomere and a viable human embryo from which the blastomere was obtained.

23. The method of claim 22, wherein the remaining human embryo is cryopreserved following obtaining the blastomere.

24. The method of claim 17, wherein the blastomere is obtained by immobilizing the embryo and tapping the immobilized embryo until the blastomere is isolated.

25. The method of claim 17, further comprising performing genetic testing on at least one progeny cell of said blastomere.

26. The method of claim 17, wherein step (b) comprises culturing in a medium containing less than 5 mM glucose and having an osmolarity less than 310 mOsm/k.

* * * * *